US011077080B2

(12) United States Patent
Mouthon et al.

(10) Patent No.: US 11,077,080 B2
(45) Date of Patent: Aug. 3, 2021

(54) USE OF ANTI-CONNEXIN AGENTS FOR MODULATING THE THERAPEUTIC EFFECT OF PSYCHOTROPIC DRUGS

(71) Applicants: Commissariat A L'Energie Atomique Et Aux Energies Alternatives, Paris (FR); Bio Modeling Systems Ou Bmsystems, Paris (FR)

(72) Inventors: Franck Mouthon, Paris (FR); Mathieu Charveriat, Issy les Moulineaux (FR); Jean-Philippe Deslys, Le Chesnay (FR); François Iris, Chaville (FR)

(73) Assignees: COMMISSARIAT A L'ENERGIE ATOMIQUE AUX ENERGIES ALTERNATIVES, Paris (FR); BIO MODELING SYSTEMS OU BMSYSTEMS, Paris (FR)

( * ) Notice: Subject to any disclaimer, the term of this patent is extended or adjusted under 35 U.S.C. 154(b) by 0 days.

(21) Appl. No.: 14/736,004

(22) Filed: Jun. 10, 2015

(65) Prior Publication Data
US 2015/0272915 A1 Oct. 1, 2015

Related U.S. Application Data

(62) Division of application No. 13/063,409, filed as application No. PCT/EP2009/061765 on Sep. 10, 2009, now abandoned.

(30) Foreign Application Priority Data

Sep. 10, 2008 (FR) ...................... 0856090

(51) Int. Cl.
| *A01N 43/00* | (2006.01) |
| *A01N 43/46* | (2006.01) |
| *A61K 31/55* | (2006.01) |
| *A61K 31/196* | (2006.01) |
| *A61K 31/4525* | (2006.01) |
| *A61K 31/5513* | (2006.01) |
| *A61K 31/551* | (2006.01) |
| *A61K 31/165* | (2006.01) |
| *A61K 31/135* | (2006.01) |
| *A61K 31/137* | (2006.01) |
| *A61K 31/343* | (2006.01) |
| *A61K 31/56* | (2006.01) |
| *A61K 45/06* | (2006.01) |

(52) U.S. Cl.
CPC .......... *A61K 31/196* (2013.01); *A61K 31/135* (2013.01); *A61K 31/137* (2013.01); *A61K 31/165* (2013.01); *A61K 31/343* (2013.01); *A61K 31/4525* (2013.01); *A61K 31/551* (2013.01); *A61K 31/5513* (2013.01); *A61K 31/56* (2013.01); *A61K 45/06* (2013.01)

(58) Field of Classification Search
None
See application file for complete search history.

(56) References Cited

U.S. PATENT DOCUMENTS

2005/0107349 A1* 5/2005 Seibert ................ A61K 31/495
514/165

FOREIGN PATENT DOCUMENTS

| WO | WO 2005046667 A2 * | 5/2005 | .......... A61K 31/198 |
| WO | WO 2005084654 A2 * | 9/2005 | ............ A61K 31/00 |
| WO | WO 2007/002139 A2 | 1/2007 | |
| WO | WO 2007/062186 A2 | 5/2007 | |

OTHER PUBLICATIONS

Alldredge, "Clinical connexions", J. Clin. Pathol., vol. 61, pp. 885-890, 2008 (Published online May 12, 2008).
Bai et al., "Block of Specific Gap Junction Channel Subtypes by 2-Aminoethoxydiphenyl Borate (2-APB)", The Journal of Pharmacology and Experimental Therapeutics, vol. 319, No. 3, pp. 1452-1458, 2006.
Burt et al., "Volatile Anesthetics Block Intercellular Communication Between Neonatal Rat Myocardial Cells", Circulation Research, vol. 65, No. 3, pp. 829-837, Sep. 1989.
Chaytor et al., "Peptides homologous to extracellular loop motifs of connexin 43 reversibly abolish rhythmic contractile activity in rabbit arteries", Journal of Physiology, vol. 503.1, pp. 99-110, 1997.
Dahl et al., "Attempts to Define Functional Domains of Gap Junction Proteins with Synthetic Peptides", Biophysical Journal, vol. 67, pp. 1816-1822, Nov. 1994.
De Saint Hilaire et al., "Variations in extracellular monoamines in the prefrontal cortex and medial hypothalamus after modafinil administration: a microdialysis study in rats", NeuroReport, vol. 12, No. 16, pp. 3533-3537, Nov. 16, 2001.
(Continued)

Primary Examiner — Layla Soroush
(74) Attorney, Agent, or Firm — Birch, Stewart, Kolasch & Birch, LLP

(57) ABSTRACT

The invention first relates to a product containing at least one connexin-blocking agent and a psychotropic drug as combination products for use simultaneously, separately, or spread over time in patients suffering from psychiatric and/or neurodegenerative disorders. The connexin-blocking agent is advantageously selected from the group comprising meclofenamic acid, 18-β-glycyrrhetinic acid, carbenoxolone, mefloquine, and 2-APB, and preferably consists of meclofenamic acid. The invention first relates to a product containing at least one connexin-blocking agent and a psychotropic drug as combination products for use simultaneously, separately, or spread over time in patients suffering from psychiatric and/or neurodegenerative disorders. The connexin-blocking agent is advantageously selected from the group comprising meclofenamic acid, 18-β-glycyrrhetinic acid, carbenoxolone, mefloquine, and 2-APB, and preferably consists of meclofenamic acid.

3 Claims, 13 Drawing Sheets

(56) References Cited

OTHER PUBLICATIONS

Dimpfel, "Characterization of atypical antipsychotic drugs by a late decrease of striatal alphal spectral power in the electropharmacogram of freely moving rats", British Journal of Pharmacology, vol. 152, pp. 538-548, 2007 (Published online Aug. 13, 2007).
Fabrizi et al., "Charcot-Marie-Tooth disease type 2E, a disorder of the cytoskeleton", Brain, vol. 130, pp. 394-403, 2007 (Advance Access publication Oct. 18, 2006).
Fatemi et al., "Chronic psychotropic drug treatment causes differential expression of connexin 43 and GFAP in frontal cortex of rats", Schizophrenia Research, vol. 104, pp. 127-134, 2008, XP024523139 (Published online Jun. 27, 2008).
Figueroa et al., "Histamine reduces gap junctional communication of human tonsil high endothelial cells in culture", Microvascular Research, vol. 68, pp. 247-257, 2004 (Published online Aug. 27, 2004).
Freo et al., "Cerebral metabolic effects of fluoxetine, fluvoxamine, paroxetine and sertraline in the conscious rat", Neuroscience Letters, vol. 436, pp. 148-152, 2008.
Fukuda, "Structural Organization of the Gap Junction Network in the Cerebral Cortex", The Neuroscientist, vol. 13, No. 3, pp. 199-207, 2007.
Galderisi, "Clinical Applications of Pharmaco-EEG in Psychiatry: The Prediction of Response to Treatment with Antipsychotics", Methods Find. Exp. Clin. Pharmacol., vol. 24 (Suppl. A), pp. 85-89, 2002.
Gareri et al., "Influence of carbenoxolone on the anticonvulsant efficacy of conventional antiepileptic drugs against audiogenic seizures in DBA/2 mice", European Journal of Pharmacology, vol. 484, pp. 49-56, 2004.
Giepmans, "Gap junctions and connexin-interacting proteins", Cardiovascular Research, vol. 62, pp. 233-245, 2004.
Guan et al., "The Sleep-inducing Lipid Oleamide Deconvolutes Gap Junction Communication and Calcium Wave Transmission in Glial Cells", The Journal of Cell Biology, vol. 139, No. 7, pp. 1785-1792, Dec. 29, 1997.
Harks et al., "Fenamates: A Novel Class of Reversible Gap Junction Blockers", The Journal of Pharmacology and Experimental Therapeutics, vol. 298, No. 3, pp. 1033-1041, 2001.
Henshall et al., "Electroencephalographic and behavioral convulsant effects of hydrobromide and hydrochloride salts of bupropion in conscious rodents", Neuropsychiatric Disease and Treatment, vol. 5, pp. 189-206, 2009.
Hofer et al., "Visualization and Functional Blocking of Gap Junction Hemichannels (Connexons) With Antibodies Against External Loop Domains in Astrocytes", GLIA, vol. 24, pp. 141-154, 1998.
International Search Report and Written Opinion of the International Searching Authority, dated Dec. 3, 2009, for Application No. PCT/EP2009/061765.
Kola et al., "Can the pharmaceutical industry reduce attrition rates?", Nature Reviews, Drug Discovery, vol. 3, pp. 711-715, Aug. 2004.
Lai-Cheong et al., "Genetic Diseases of Junctions", Journal of Investigative Dermatology, vol. 127, pp. 2713-2725, 2007.
Locke et al., "Reversible Pore Block of Connexin Channels by Cyclodextrins", The Journal of Biological Chemistry, vol. 279, No. 22, pp. 22883-22892, May 28, 2004.
Mandema et al., "Electroencephalogram Effect Measures and Relationships Between Pharmacokinetics and Pharmacodynamics of Centrally Acting Drugs", Clin. Pharmacokinet., vol. 23, No. 3, pp. 191-215, 1992.
Meda, "Connexines, canaux jonctionnels et communications cellulaires", Médecine/Sciences, vol. 12, No. 8-9, pp. 909-920, Aug.-Sep. 1996.
Meyer et al., "Inhibition of Gap Junction and Adherens Junction Assembly by Connexin and A-CAM Antibodies", The Journal of Cell Biology, vol. 119, No. 1, pp. 179-189, Oct. 1, 1992.
Negri et al., "Impaired Nociception and Inflammatory Pain Sensation in Mice Lacking the Prokineticin Receptor PKR1: Focus on Interaction between PKR1 and the Capsaicin Receptor TRPV1 in Pain Behavior", The Journal of Neuroscience, vol. 26, No. 25, pp. 6716-6727, Jun. 21, 2006.
Pan et al., "Screening of gap junction antagonists on dye coupling in the rabbit retina", Vis. Neurosci., vol. 24, No. 4, pp. 609-618 (20 page NIH Public Access re-publication provided), 2007.
Paranjape et al., "Habituation of insulin-induced hypoglycemic transcription activation of lateral hypothalamic orexin-A-containing neurons to recurring exposure", Regulatory Peptides, vol. 135, pp. 1-6, 2006 (Published online May 5, 2006).
Postma et al., "Acute loss of Cell-Cell Communication Caused by G Protein-coupled Receptors: A Critical Role for c-Src", The Journal of Cell Biology, vol. 140, No. 5, pp. 1199-1209, Mar. 9, 1998.
Robledo et al., "Effects of MK 801 and Diazepam on the EEG of P and NP Rats", Alcoholism: Clinical and Experimental Research, vol. 18, No. 2, pp. 363-368, Mar./Apr. 1994.
Salameh et al., "Pharmacology of Gap junctions. New pharmacological targets for treatment of arrhythmia, seizure and cancer?", Biochimica et Biophysica Acta, vol. 1719, pp. 36-58, 2005 (Published online Sep. 21, 2005).
Salin-Pascual et al., "Effects of venlafaxine in the sleep architecture of rats", Psychopharmacology, vol. 129, pp. 295-296, 1997.
Sánchez et al., "Depression and poor sleep: The effect of monoaminergic antidepressants in a pre-clinical model in rats", Pharmacology, Biochemistry and Behavior, vol. 86, pp. 468-476, 2007 (Published online Jan. 18, 2007).
Scemes, "Modulation of Astrocyte P2Y1 Receptors by the Carboxyl Terminal Domain of the Gap Junction Protein Cx43", GLIA, vol. 56, pp. 145-153, 2008 (Published online Nov. 7, 2007).
Sebban et al., "Contrasting EEG profiles elicited by antipsychotic agents in the prefrontal cortex of the conscious rat: antagonism of the effects of clozapine by modafinil", British Journal of Pharmacology, vol. 128, pp. 1055-1063, 1999.
Shaw et al., "Microtubule Plus-End-Tracking Proteins Target Gap Junctions Directly from the Cell Interior to Adherens Junctions", Cell, vol. 128, pp. 547-560, Feb. 9, 2007.
Srinivas et al., "Closure of Gap Junction Channels by Arylaminobenzoates", Molecular Pharmacology, vol. 63, No. 6, pp. 1389-1397, 2003.
Srinivas et al., "Quinine blocks specific gap junction channel subtypes", PNAS, vol. 98, No. 19, pp. 10942-10947, Sep. 11, 2001.
Tejwani et al., "Inhibition of morphine tolerance and dependence by diazepam and its relation to µ-opioid receptors in the rat brain and spinal cord", Brain Research, vol. 797, pp. 305-312, 1998.
Turner et al.: "Modafinil improves cognition and response inhibition in adult attention-deficit/hyperactivity disorder", Biological psychiatry 55.10 (2004): 1031-1040.
Urbano et al.: "Modafinil enhances thalamocortical activity by increasing neuronal electrotonic coupling", Proc Natl Acad Sci USA. Jul. 24, 2007; 104(30): 12554-12559.
Wellershaus et al., "A new conditional mouse mutant reveals specific expression and functions of connexin36 in neurons and pancreatic beta-cells", Experimental Cell Research, vol. 314, pp. 997-1012, 2008 (Published online Jan. 12, 2008).
Winneker et al., "The preclinical biology of a new potent and selective progestin: trimegestone", Steroids, vol. 68, pp. 915-920, 2003.
Yao et al., "Nitric Oxide-Mediated Regulation of Connexin43 Expression and Gap Junctional Intercellular Communication in Mesangial Cells", J. Am. Soc. Nephrol., vol. 16, pp. 58-67, 2005.
Yao et al., "PDGF regulates gap junction communication and connexin43 phosphorylation by PI 3-kinase in mesangial cells", Kidney International, vol. 57, pp. 1915-1926, 2000.

* cited by examiner

Hour 1

─△─ Anti-connexin (0.4 mg/kg)
─○─ Modafinil (125 mg/kg)
─■─ Combination of Modafinil + Anti-connexin
‧‧‧•‧‧‧ Modafinil (250 mg/kg)

Hour 2

USE OF ANTI-CONNEXIN AGENTS FOR MODULATING THE THERAPEUTIC EFFECT OF PSYCHOTROPIC DRUGS

CROSS REFERENCE TO RELATED APPLICATIONS

This application is a Divisional Application of co-pending U.S. application Ser. No. 13/063,409, filed on Mar. 10, 2011, which is the National Phase of PCT International Application No. PCT/EP2009/061765 filed on Sep. 10, 2009, which claims priority under 35 U.S.C. § 119(a) to Patent Application No. 0856090, filed in FRANCE on Sep. 10, 2008, all of which are hereby expressly incorporated by reference into the present application.

This invention relates to improvements in therapeutic neurological and neuropsychic treatments using psychotropic molecules. More specifically, the invention enables the effects of psychotropic drugs to be modulated and/or potentiated by certain molecules, referred to here as anti-connexin agents.

The development and use of molecules for therapeutic purposes targeting the central nervous system represent a rapidly developing field. This development is nevertheless faced with numerous limitations:

adverse effects may appear at the therapeutic dose and therefore reduce the therapeutic benefits, resistance to treatment, intolerance to treatment, treatment failure and addition phenomena are among the individual reactions to the drugs, which are particularly limiting in the development and clinical use of psychotropic molecules, the fact that therapeutic effects are offset with respect to the time of administration, a phenomenon that is fully documented in the context of antidepressant treatments, is a source of considerable uncertainty in adapting the dosage.

Moreover, among the possible molecules for the treatment of central nervous system pathologies, only 8% are validated in clinical trials and are then placed on the market. In preclinical trials, 20% of the molecules are rejected due to toxicology results that are unacceptable for treatment in humans (Kola I, *Nat Rev Drug Discov.* 2004 Aug. 3(8): 711-5). These molecules could nevertheless have a therapeutic effect if their action could be potentiated by one or more other molecules.

In this context, it is therefore important to find means to (i) best control the therapeutic limitations and the adverse effects and (ii) improve the efficacy of the molecules intended to treat pathologies of the central nervous system.

Various studies have already addressed the modulation of the adverse effects of treatments. The few attempts described have largely related to molecules or peptides targeting receptors:

PKR1 in nociception phenomena (Negri L, *The Journal of Neuroscience*, 2006 Jun. 21; 26(25): 6716-27)), a non-steroidal glucocorticoid receptor antagonist in the case of extreme hypoglycemia after chronic insulin treatment (Kale A Y 2006, *Brain Research* Bulletin 2006 Jul. 15; 135(1-2): 1-6), trimegestone, a progesterone receptor agonist that partially counteracts the adverse effects of estradiol treatments without compromising their efficacy in the treatment of osteoporosis (Winneker R C, *Steroids*, 2003 November; 68 (10-13): 915-20), diazepam, a GABAA receptor agonist, for attenuating the addictive effects of opiates (Tejwani G A, *Brain Res.* 1998 Jun. 29; 797(2): 305-12).

In general, at the time of the invention, the approaches intended to solve the problems associated with the use of psychotropic drugs have involved intervention not on a general control system, but instead on certain specific receptors.

alone, the connexin inhibitor (Meclofenamic acid 0.4 mg/kg by intraperitoneal injection) alone, or the combination of Modafinil (125 mg/kg intraperitoneally) and connexin inhibitor. The x-axis shows the frequencies analyzed and the y-axis shows the relative powers obtained from the FFT analysis. The spectral analysis is shown as an average for the 6 animals for the first hour and for the second hour.

Figure 8:
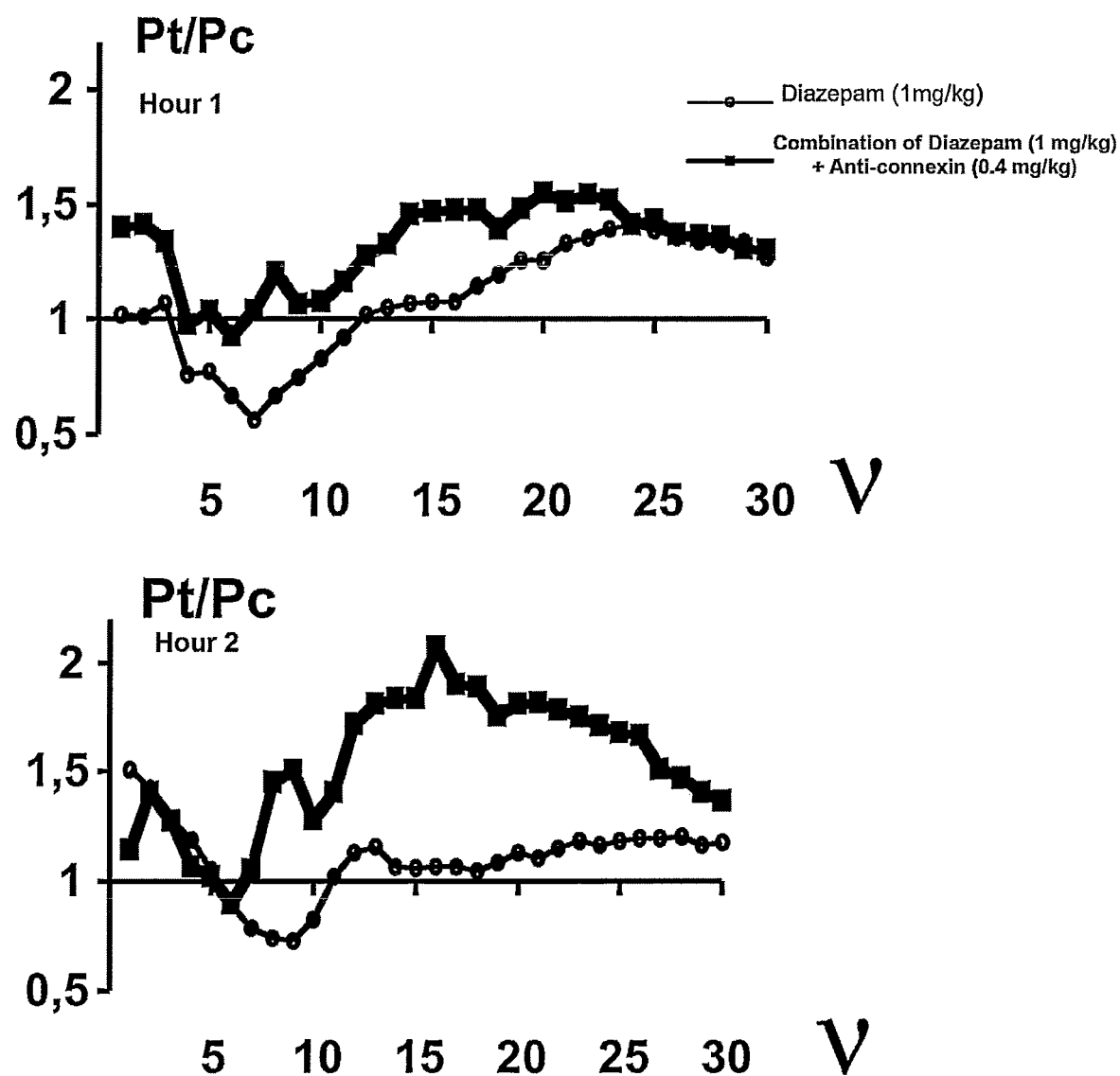

FIG. 8 shows the spectral analysis of the electrical activity of the prefrontal cortex by quantitative EEG of the effect of Diazepam (1 mg/kg intraperitoneally) alone, or the combination of Diazepam (1 mg/kg intraperitoneally) with the connexin inhibitor (Meclofenamic acid, 0.4 mg/kg intraperitoneally). The x-axis shows the frequencies analyzed and the y-axis shows the relative powers obtained from the FFT analysis. The spectral analysis is shown as an average for the 6 animals for the first hour and for the second hour.

Figure 9:
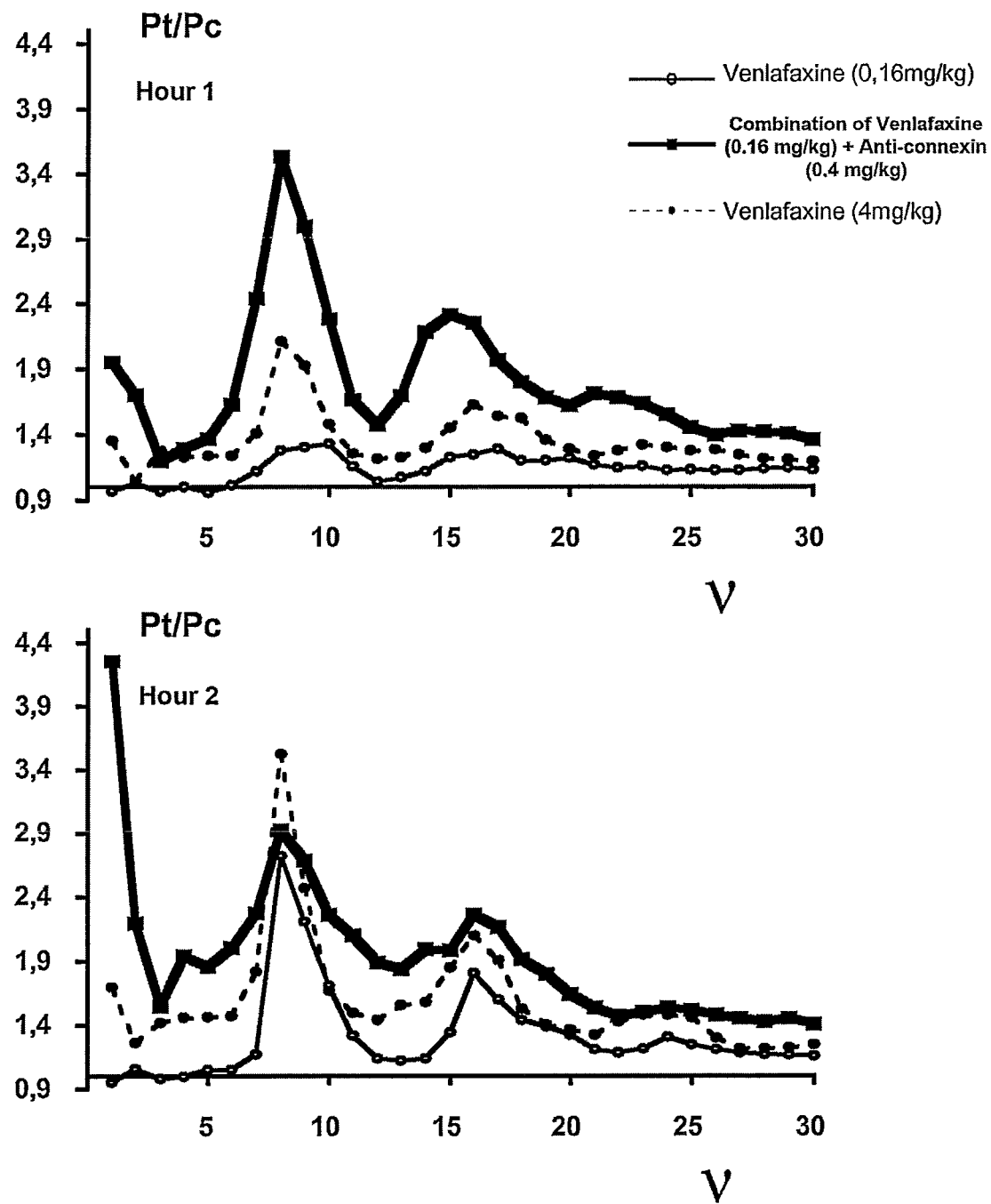

FIG. 9 shows the spectral analysis of the electrical activity of the prefrontal cortex by quantitative EEG of the effect of Venlafaxine (0.16 mg/kg and 4 mg/kg intraperitoneally) alone, or the combination of Venlafaxine (0.16 mg/kg intraperitoneally) with the connexin inhibitor (Meclofenamic acid, 0.4 mg/kg intraperitoneally). The x-axis shows the frequencies analyzed and the y-axis shows the relative powers obtained from the FFT analysis. The spectral analysis is shown as an average for the 6 animals for the first hour and for the second hour.

Figure 10:
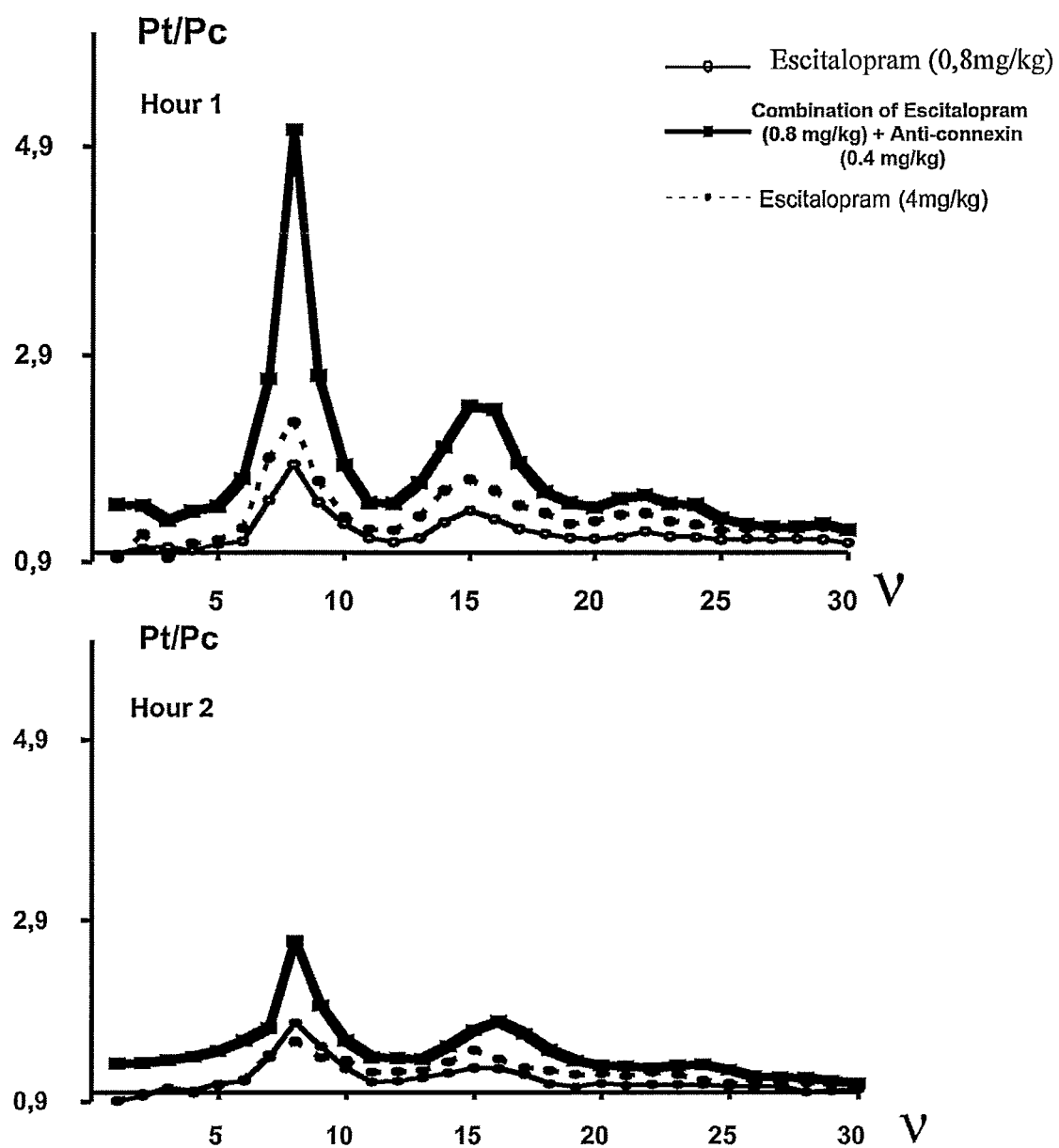

FIG. 10 shows the spectral analysis of the electrical activity of the prefrontal cortex by quantitative EEG of the effect of Escitalopram (0.8 mg/kg and 4 mg/kg intraperitoneally) alone, or the combination of Escitalopram (0.8 mg/kg intraperitoneally) with the connexin inhibitor (Meclofenamic acid, 0.4 mg/kg intraperitoneally). The x-axis shows the frequencies analyzed and the y-axis shows the relative powers obtained from the FFT analysis. The spectral analysis is shown as an average for the 6 animals for the first hour and for the second hour.

Figure 11:
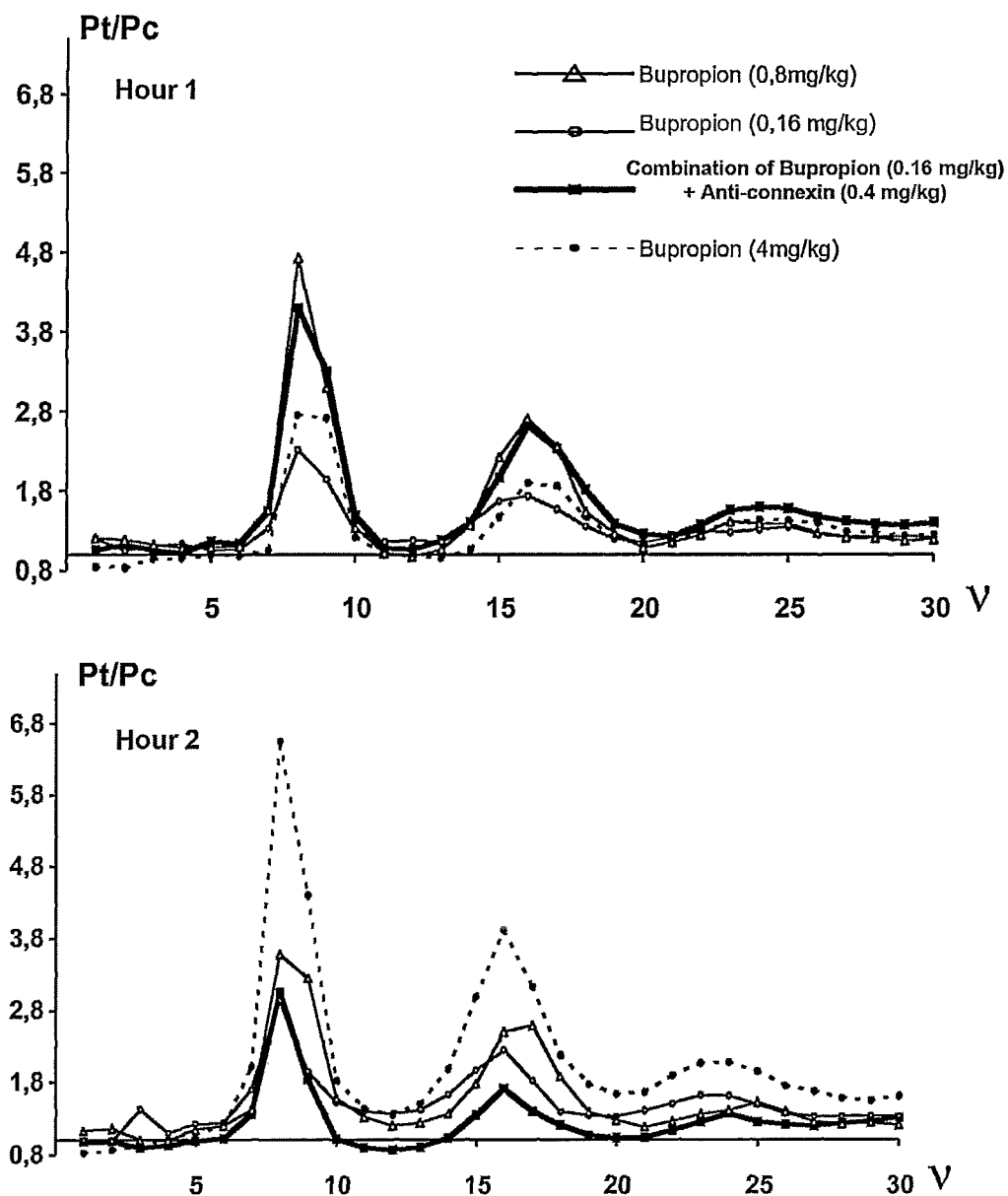

FIG. 11 shows the spectral analysis of the electrical activity of the prefrontal cortex by quantitative EEG of the effect of Bupropion (0.16 mg/kg, 0.8 mg/kg and 4 mg/kg intraperitoneally) alone, or the combination of Bupropion (0.16 mg/kg intraperitoneally) with the connexin inhibitor (Meclofenamic acid, 0.4 mg/kg intraperitoneally). The x-axis shows the frequencies analyzed and the y-axis shows the relative powers obtained from the FFT analysis. The spectral analysis is shown as an average for the 6 animals for the first hour and for the second hour.

Figure 12:
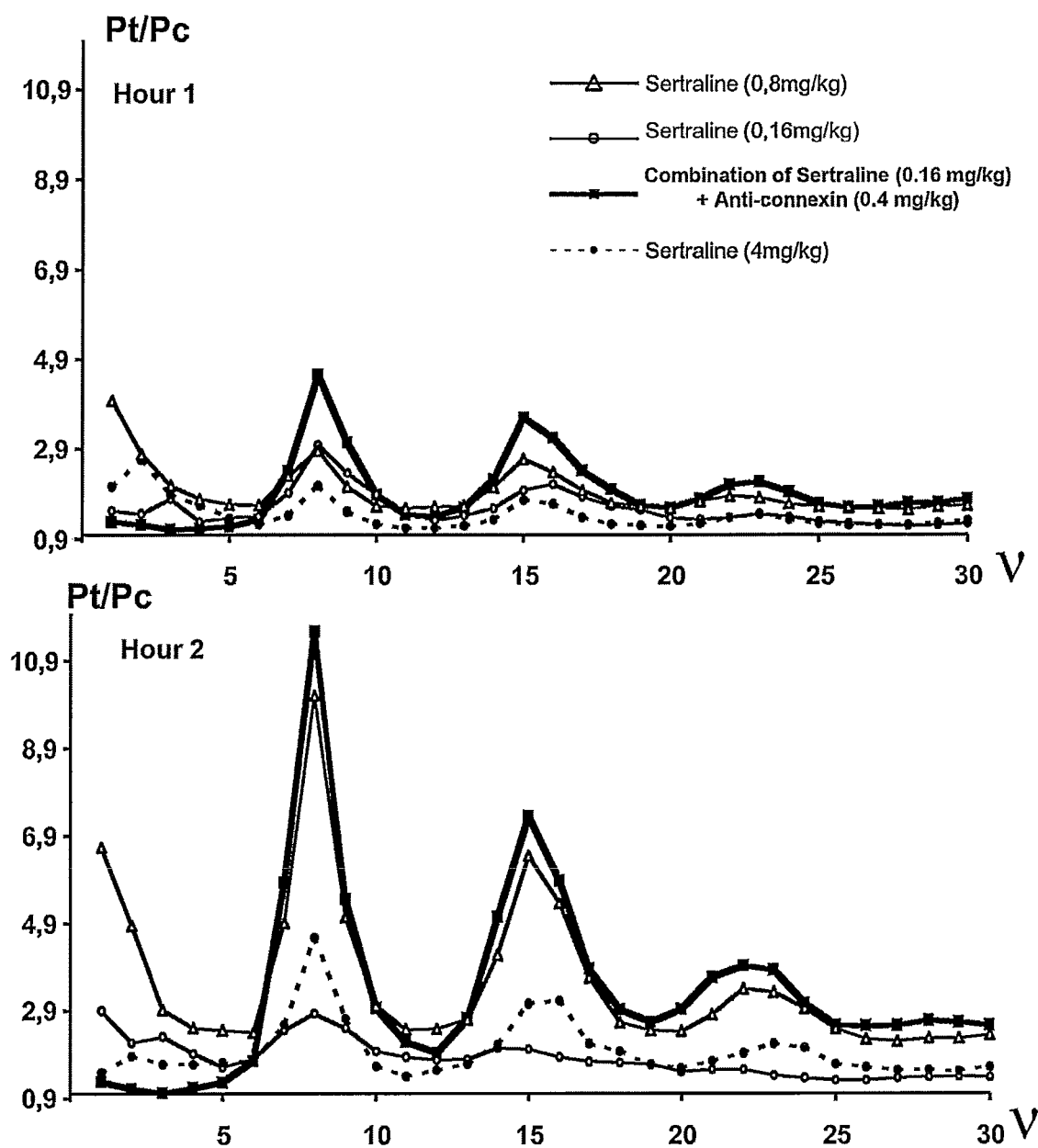

FIG. 12 shows the spectral analysis of the electrical activity of the prefrontal cortex by quantitative EEG of the effect of Sertraline (0.16 mg/kg, 0.8 mg/kg and 4 mg/kg intraperitoneally) alone, or the combination of Sertraline (0.16 mg/kg intraperitoneally) with the connexin inhibitor (Meclofenamic acid, 0.4 mg/kg intraperitoneally). The x-axis shows the frequencies analyzed and the y-axis shows the relative powers obtained from the FFT analysis. The spectral analysis is shown as an average for the 6 animals for the first hour and for the second hour.

Figure 13:
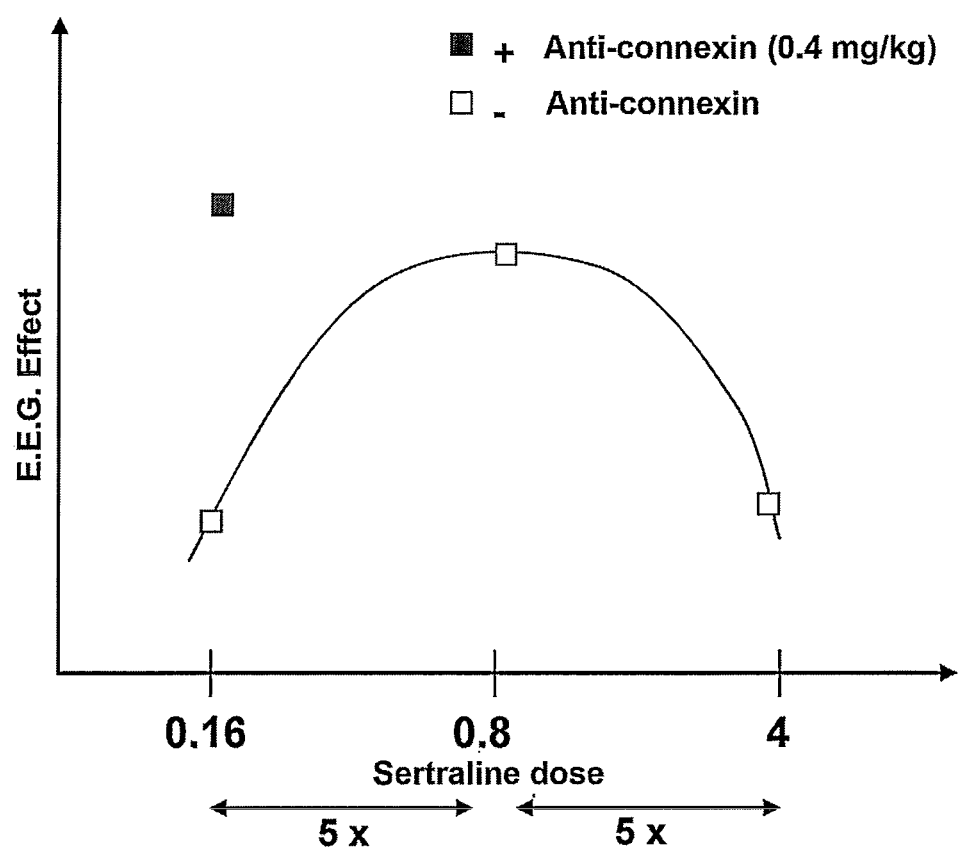

FIG. 13 shows a diagrammatic representation of the EEG effect in the form of an inverted "U" for sertraline alone according to the dose administered over the two recording hours (0.16 mg/kg, 0.8 mg/kg and 4 mg/kg intraperitoneally) alone, or the combination of Sertraline (0.16 mg/kg intraperitoneally) with the connexin inhibitor (Meclofenamic acid, 0.4 mg/kg intraperitoneally).

DESCRIPTION OF THE INVENTION

Intercellular communication is important for maintaining tissue and organ homeostasis. To establish this communication, gap junctions connect the cell cytoplasm, enabling the exchange of ions ($Ca^+$ and $K^+$), second messengers (AMPc, GMPc, IP3), several small metabolites (glucose) and ensuring electrical and metabolic coupling between the cells. The gap junctions are junctions with a selective permeability, formed by protein channels contained in the plasma membrane, and formed by connexin hexamers (Meda P, *Médecine/Sciences* 1996; 12: 909-920).

Connexins are integral proteins of the plasma membrane, which are synthesized by practically every cell type, regardless of the position of a multicellular organism in the phylogenesis of the animal world. In vertebrates, occasional cells not producing connexins are adult striated muscle cells, spermatozoids and circulating blood cells. Unlike numerous membrane proteins, connexins have a short half-life (between 3 and 6 hours), are not glycosylated and do not have an enzymatic activity. At present, at least thirteen distinct connexins have been identified in mammals; corresponding, in humans, to 21 isoforms. In practice, various types of connexin can be present in a plurality of tissues, and most of the cells synthesize a plurality of connexins (Meda P, *Médecine/Sciences* 1996; 12: 909-920). Before reaching the cell membrane, the connexins assembly in groups of six molecules to form hollow tubular structures called connexons, which join the plasma membrane by means of Golgi vesicles. When cell contact is established, the connexons of a cell align end-to-end with those of the neighboring cell, establishing a continuous hydrophilic channel around 10 nm long. This junctional channel establishes direct contact between the cytoplasms of the two cells in contact, over the intercellular space.

Thus, the formation of hexamer duplexes between two adjacent plasma membranes constitutes the gap junction. There are 21 genes coding for different connexin isoforms in humans, and different combinations of connexin monomers involved in the composition of the gap junctions are described. Half of the connexins identified are expressed in the brain, and more specifically connexin 36 (Cx36), which appears to be predominantly expressed by neurons, in an interface defined as the electrical synapse. Mice deficient in connexin 36 do not have any inter-neuron coupling, which helps to confirm the leading role of these particular connexins in at least one type of electrical synapse (Wellershaus K, *Exp Cell Res.* 2008).

The electrical synapses do not transmit information faster than chemical synapses, but have a particular characteristic, that of reciprocity: neither inhibiting nor excitatory, they locally synchronize the state of multiple cells, and bilaterally. The gap junctions acting as low pass filters, this process of normalization of the state of the cells is more effective as it involves more or less long-term changes. Electrical couplings between neurons, owing to their characteristics, would play a role in oscillation phenomena and rhythmic discharges in the neocortex and the hippocampus.

Finally, connexins are present everywhere in the different brain structures and are involved locally in the oscillations of electrical activities.

However, the present inventors recently demonstrated that connexins also play an important role in the general regulation of the electrical activity of the brain. Surprisingly, when they are physiologically present, these proteins indeed have a general desynchronizing role on the electrical activity of the CNS, damping and potentially neutralizing burst phenomena. Conversely, the inhibition of these molecules by means of so-called "anti-connexin" agents makes it possible to synchronize and therefore increase the electrophysiological activity measured.

As it is known that the increase in the electrical activity of the CNS, measured on an electroencephalogram (EEG), reflects, under certain conditions, the therapeutic effects of a psychotropic drug (Galderisi S, *Methods Find Exp Clin Pharmacol*, 2002, 24, 85-89), the present inventors had the idea of testing the effect of the inhibition of connexins on the therapeutic effect associated with the administration of psychotropic drugs.

Their numerous results clearly prove that the modulation of the cerebral electrical activity associated with the administration of anti-connexin agents makes it possible to obtain a psychotropic drug dose benefit with which the agents are associated and to have a method for evaluating this dose benefit based on this modulation. The combination of an anti-connexin agent with a psychotropic molecule, for example an antidepressant, therefore makes it possible (i) to increase the specificity of action and the therapeutic effects of the psychotropic molecule, and (ii) to reduce the active doses and thus reduce the indirect effects of these psychotropic molecules (undesirable effects, failure, resistance).

According to a first aspect, this invention proposes a method for evaluating the effective psychotropic drug equivalent dose that may be combined with the connexin blocking agent in the treatment of a patient suffering from psychiatric and/or neurodegenerative disorders. This combination is intended to obtain the same therapeutic effect as that of the psychotropic drug alone administered at a stronger dose, but with fewer adverse effects.

In the context of the invention, the "effective equivalent dose" of a psychotropic drug refers to the psychotropic drug dose that, when administered in combination with the connexin blocking agent, induces a physiological effect or a pharmacological signature similar or identical to that of the psychotropic drug alone administered at the active pharmacological dose.

In addition, the "pharmacologically active dose" of a psychotropic drug refers to the psychotropic drug dose classically administered to laboratory animals such as rats, mice, rabbits and so on. Such doses are provided, for example, in *Animal models in psychopharmacology*. Olivier B, Slangen J, Mos J, eds. Birkhauser Verlag, Basel; 1991. If this dose is not known, it is possible to determine the pharmacologically active dose of the psychotropic drug by transposing, in the animal, the pharmacologically active doses classically prescribed in humans and that can be consulted in "Médicaments psychotropes: consommation et pratiques de prescription en France métropolitaine. I. Données nationales, 2000", Lecadet J, Vidal P, Baris B et al.; Revue Médicale de l'Assurance Maladie volume 34 no. 2/April-June 2003". It is also possible to determine this pharmacologically active dose by experimental tests, in which the pharmacologically active dose is the maximum psychotropic drug dose that can be administered to an animal without the adverse effects becoming more pronounced than the therapeutic effect. In this case, the pharmacologically active dose can be determined cumulatively by administering a plurality of psychotropic drug doses at increasing doses and by measuring, each time, the effect produced by said drug.

In the context of this invention, a "connexin-blocking" agent is a chemical molecule, a protein, a protein fragment or a nucleic acid (RNAi) capable of inhibiting the functional activity of connexins, directly and/or indirectly, and more generally any type of intercellular junctions, and/or capable of functionally inhibiting, directly and/or indirectly any cellular activity involving a connexin-type protein. Such an agent can also be referred to as an "anti-connexin molecule".

The method for evaluating the effective equivalent dose of a psychotropic drug is based on the quantification of the potentiation of the effect of the psychotropic drug by the agent blocking the connexins. This evaluation is performed in several steps: a step of characterization of the effects specific to the psychotropic agent and a step of measuring the dose benefit of the combination product. The first step consists of determining and quantifying the effects of the psychotropic drug alone at different doses (pharmacologically active dose and doses decreasing from the pharmacologically active dose), and thus having signatures specific to the psychotropic molecule—or standard signatures—at the different doses. The second step consists of determining the psychotropic drug dose, which, administered in combination with the connexin-blocking agent, has the same pharmacological signature as the psychotropic drug alone.

Advantageously, the dose of connexin-blocking agent used in combination with the psychotropic drug is first determined by experimental tests. This dose indeed corresponds to the maximum dose of connexin-blocking agent that can be administered without producing a significant specific pharmacological effect. This dose can be adjusted when implementing the method according to the invention so as to optimize the effect of the combination.

The method for evaluating the effective equivalent dose of a psychotropic drug according to the invention includes the following steps:

a) having as many animal groups as there are experimental conditions to be tested, b) administering, to a first animal group, a pharmacologically active dose of said psychotropic drug, and, to successive animal groups, doses decreasing from said pharmacologically active dose, c) characterizing, in the animals of said groups, the effect produced by said psychotropic drug at the different doses administered, d) administering, to new animal groups, said combination product containing said psychotropic drug at the doses used in b), and said connexin-blocking agent, e) characterizing, in the animals of said groups, the effect produced by each of said combination products administered in d), f) determining the effective equivalent dose of the psychotropic drug, i.e. the dose of psychotropic drug that, when administered in combination with the connexin-blocking agent, produces the same effect as that of the psychotropic drug alone administered at said pharmacologically active dose.

This method for evaluating the effective equivalent dose of a psychotropic drug also makes it possible to evaluate the dose benefit between a combination product combining said psychotropic drug at the effective equivalent dose and a connexin-blocking agent and the psychotropic drug administered at the pharmacologically active dose.

The term "dose benefit" refers, in this application, to the ratio between the pharmacological dose of the psychotropic drug alone and the effective equivalent dose of the psychotropic drug. In other words, the dose benefit explains by how much the pharmacological dose of a prescribed psychotropic drug can be reduced in view of its combination with the anti-connexin agent. This reduction in the psychotropic drug dose administered (in combination with the anti-connexin molecules) will not have any consequence in terms of efficacy of the treatment, but will reduce adverse effects.

Thus, the dose benefit defined above can be written as:

$$DB = \frac{\text{Pharmacologically active dose of the psychotropic drug}}{\text{Effective equivalent dose of the psychotropic drug}}$$

It is understood that, to perform the evaluation method according to the invention, said animal groups are of the same species. Moreover, each animal group receives exclusively either a dose of psychotropic drug alone, or a combination product containing a certain dose of psychotropic drug and an anti-connexin agent, so as to measure, in the animals of the same group, only the effect of said drug or of said combination product alone. Preferably, said animal groups are the same age and same sex. These animals are preferably laboratory animals, for example rats, mice, rabbits and so on.

It is understood that the number of doses to be tested is determined according to the pharmacological effect of the psychotropic drug or of the combination product combining the psychotropic drug and the connexin-blocking agent; when the pharmacological effect produced by a certain dose is non-existent or insignificant, it is no longer necessary to use lower doses.

The administration of the drug or of the combination product can be performed intracerebrally, but is preferably performed intraperitoneally.

Advantageously, the effect produced by the psychotropic drug and/or the combination product can be determined by different types of analysis, in particular an electrophysiological or behavioral analysis or blood markers or LCR markers, or by medical imaging. Preferably, this effect is determined by reference to an electrophysiological response resulting from a given stimulation, in particular in reference to the electroencephalographic activity (EEG) of the animal.

Advantageously, this evaluation method makes it possible to define the optimal time scheme for administration of the two elements of the combination product (simultaneous, separate or sequential administration).

This evaluation method also makes it possible to make a selection with regard to the nature of the connexin-blocking agent, to the psychotropic drug, as well as to the doses used.

According to a second aspect, this invention relates to a new combination product containing at least one connexin-blocking agent and a psychotropic drug, and the use thereof in patients with psychiatric and/or neurodegenerative disorders.

Various molecules are known for blocking the gap junctions via connexins.

Among them, the family of fenamates includes the following compounds: meclofenamic acid, flufenamic acid, niflumic acid and tolfenamic acid. These compounds all have a non-steroidal anti-inflammatory activity, but this activity is not responsible for their capacity to block the gap junctions. It has indeed been suggested that the fenamates instead establish a direct interaction with the connexins or with the protein membrane interfaces that may influence the conformation of the connexins and therefore the functional role thereof (Harks E G, *The Journal of Pharmacology and Experimental Therapeutics* 2001 September, 298(3): 1033-41).

Benzoic 2-[(2,6-di-chloro-3-phenyl)amino] acid, more commonly known as meclofenamic acid (MFA), is a non-steroidal anti-inflammatory agent and a peripheral analgesic of the fenamate class, a prostaglandin inhibitor, described among the water-soluble blockers as being the most effective for reversibly blocking the gap junctions. In addition, meclofenamic acid is not specific to a type of connexin and is therefore effective for blocking a large number of cerebral connexins (Pan F, *Vis Neurosciences* 2007, July-August; 24(4): 609-18).

Glycyrrhetinic acid derivatives refer to 18-β-glycyrrhetinic acid (BGA) also known as "enoxolone", 18-α-glycyrrhetinic acid and carbenoxolone acid, which are triterpinoid saponins known for inhibiting the 11-hydroxysteroid dehydrogenase enzyme. Moreover, these compounds are capable of very effectively inhibiting the gap junctions (Pan F, *Vis Neurosciences* 2007, July-August; 24(4): 609-18).

Mefloquine (LARIAM), of the quinine family, also has a strong antagonist power on the gap junctions (Srinivas M, *PNAS* 2001, 98: 10942-10947; Pan F, *Vis Neurosciences* 2007, July-August; 24(4):609-18).

Some anesthetic agents, such as halothane and isoflurane, have a rapid and reversible gap junction blocking effect (Burt J M, et al, *Circ Research.* 1989; 65: 829-37).

Moreover, oleamide (cis-9-octadecenamide), the first amide of oleic acid, also has an inhibiting action on the connexin molecules 43 and 32 (Guan X. et al, *J. Cell Biol* 1997; 139: 1785-92).

In addition, cyclodextrins (α-cyclodextrin (α-CD), β-cyclodextrin (β-CD) and γ-cyclodextrin (γ-CD)), which are natural cyclical oligosaccharides of α-D-glucopyranose, have proven anti-connexin properties (Locke D. et al, *J. Biol Chem* 2004; 279: 22883-92).

Finally, 2-aminoethyldiphenyl borate (2-APB) is a compound recently identified as a gap junction-blocking agent (Bai D, *J Pharmacol Exp Ther,* 2006 December; 319(3): 1452-8). This modulator of the inositol 1,4,5-triphosphate receptor however fairly specifically targets certain connexins, such as connexins 26, 30, 36, 40, 45 and 50 (Bai D, *J Pharmacol Exp Ther,* 2006 December; 319(3): 1452-8).

Similarly, other molecules have recently been proposed for blocking the extracellular connexin domain—a domain that is important for the functioning of the gap junctions. It involves in particular antibodies directed against the extracellular connexin domain (Hofer A et al, *Glia* 1998; 24: 141-54; Meyer R A, *J. Cell Biol.* 1992; 119: 179-89) or small peptides mimicking specific sequences conserved by the extracellular loops E1 and E2 of the connexins (Dahl G. et al, *Biophys J,* 1994; 67: 1816-22); in particular, the peptides corresponding to the extracellular sequences include the conserved patterns QPG and SHVR of E1 (Gap26) and the conserved pattern SRPTEK of E2 (Gap27) of the connexins are more effective for blocking the gap junctions (Chaytor A T et al, *J. Physiol* 1997; 503: 99-110).

In the context of this invention, the connexin-blocking agents are advantageously chosen from: long-chain alcohols (for example, heptanol and octanol), fenamates (for example, meclofenamic acid, flufenamic acid, niflumic acid, tolfenamic acid), arylaminobenzoates, aminosulfonates (for example taurine), glycyrrhetinic acid derivatives (for example, 18-β-glycyrrhetinic acid, 18-α-glycyrrhetinic acid and carbenoxolone), oleamides (for example, cis-9-octadecenamide), or tetraalkylammonium ions and polyamines (such as spermine and spermidine), quinine derivatives (such as mefloquine), 2-ABP, anesthetic agents (halothane or isoflurane), cyclodextrins (α-cyclodextrin (α-CD), β-cyclodextrin (β-CD), and γ-cyclodextrin (γ-CD)), antibodies directed against the extracellular domain of the connexins or peptides with conserved patterns mimicking this particular domain (in particular Gap26 and Gap27). These different molecules are specifically described in the following articles: Srivinas M, Connexins: A Guide, *Humana Press*

2009, Chapter 8, pages 207-224; Srinivas M, *Molecular Pharmacology* 2003 June, 63(6): 1389-97; Harks E G, *The Journal of Pharmacology and Experimental Therapeutics* 2001 September, 298(3): 1033-41; and Salameh A, *Biochimica et Biophysica Acta* 1719 (2005) 36-58.

Preferably, the connexin-blocking agent is included in the group including meclofenamic acid, 18-β-glycyrrhetinic acid, carbenoxolone, mefloquine and 2-APB, and more preferably in the group including meclofenamic acid, 18-β-glycyrrhetinic acid and carbenoxolone.

These compounds are provided as examples, and the invention relates to any molecule having the properties of functional blocking, direct or indirect, of the connexins or gap junctions.

Some molecules with a recognized anti-connexin function have also been described for their anti-inflammatory effect, their anesthetic effect or their effect on prostaglandin homeostasis, and therefore, by themselves have effects on the central nervous system. However, at the doses at which these molecules are used in the invention (very low doses), the activities other than anti-connexin activities are not involved in these effects. In addition, the use of low doses allows for better tissue specificity depending on the connexin composition of the tissue, because the CNS is especially rich in connexin.

Finally, it should be noted that the anti-inflammatory molecules can indirectly produce, by their action on the prostaglandin synthase, a structural modification of the connexins (the regulation of the connexin expression levels or of the phosphorylation thereof occurs in particular via PI3K and PKA, themselves dependent on the activity levels of Cox, NO and PG synthetase, targets of anti-inflammatories). This modification, in the sense of a reduction in the presence of the connexins in the junctions, indirectly causes a reduction in the functional activity of the connexins similar to a direct blocking of the connexins. Consequently, the use of these molecules will produce the desired effect (blocking of connexins) and is not an obstacle to combined use at a low dose with psychotropic agents (Yao J, Morioka T & Oite T.: *Kidney Int.* 2000; 57: 1915-26. Yao J, Hiramatsu N, Zhu Y, et al.: *J Am Soc Nephrol.* 2005; 16: 58-67; Figueroa X F, Alvina K, Martinez A D, et al.: *Microvasc Res.* 2004; 68: 247-57 Alldredge B T.: *J Clin Pathol.* May 12, 2008; Lai-Cheong J E, Arita K & McGrath J A.: *J Invest Dermatol.* 2007; 127: 2713-25, and Giepmans B N.: *Cardiovasc Res.* 2004; 62: 233-45).

Moreover, the formation of functional gap junctions can be regulated by means of connexin phosphorylation. Indeed, phosphorylation of certain protein domains of the hexamer sub-units leads to an inhibition in the functionality of the gap junctions, according to the phosphorylation site, by closing the channels or by reducing the presence at the membrane (modification of traffic and half-life of sub-units) (Scemes E, *Glia* 2008 Jan. 15, 56(2): 145-53; Postma F R, *J Cell Biol* 1998 Mar. 9, 140(5): 1199-209; Shaw R M, *Cell* 2007 Feb. 9, 128(3): 547-60; Fabrizi G M, *Brain* 2007 February, 130 (Pt2): 394-403).

Thus, molecules can have an indirect gap junction-blocking effect, via the phosphorylation levels of the connexins. They are in particular: lysophosphatidic acid, thrombin and neuropeptides, such as endothelin (Postma F R, *J Cell Biol* 1998 Mar. 9, 140(5): 1199-209).

In a preferred embodiment of the invention, the connexin-blocking agent has an indirect effect on the connexins and the gap junctions, and it is chosen from the group consisting of: lysophosphatidic acid, thrombin and neuropeptides, such as endothelin.

In a preferred embodiment of the invention, the connexin-blocking agent is neither an anesthetic agent nor an anti-inflammatory agent, nor a prostaglandin synthesis inhibitor. According to this preferred embodiment, the connexin-blocking agent is 2-amino ethoxy diphenyl borate (2-APB).

The connexin-blocking agent can advantageously improve the therapeutic effect of psychotropic drugs prescribed by a physician for treating a patient suffering from a psychiatric and/or neurodegenerative disorder. In animals, this improvement can be measured by the method for evaluating the effective equivalent dose, which is the first objective of the invention.

"Psychotropic agent" refers to any substance that acts primarily on the state of the central nervous system by modifying certain cerebral biochemical and physiological processes.

This invention differs from the prior art in that, in the combination product, therapeutic benefits produced by the connexin-blocking agent are not specific to the use of a psychotropic drug in particular, but apply similarly to numerous molecules having psychotropic effects.

Preferably, the psychotropic drugs are chosen from the dopaminergic, GABAergic, adrenergic, acetylcholinergic, serotoninergic, opioidergic, adenosinergic, ionotropic, histaminergic, IMAO, Catechol-O-methyl transferase, DOPA decarboxylase and noradrenergic psychotropic effectors.

The term "effector" refers to any substance activating or inhibiting one or more neuroreceptors, and can therefore be an agonist or an antagonist of said receptors.

According to a preferred embodiment, the psychotropic drug is a dopaminergic effector such as loxapine, acepromazine, methylphenidate, amantadine, pergolide, lisuride, bromocriptine, ropinirole, apomorphine, aripiprazole, sulpiride, amisulpride, sultopride, tiapride, pimozide, risperidone, haloperidol, penfluridol, zuclopenthixol or bupropion.

According to another specific embodiment, the psychotropic drug is a GABAergic effector such as tiagabine, topiramate, clorazepate, diazepam, clonazepam, oxazepam, lorazepam, bromazepam, lormetazepam, nitrazepam, clotiazepam, aiprozolam, estazolam, triazolam, loprazolam, etifoxin, meprobamate, zopiclone, zolpidem, phenobarbital, felbamate or vigabatrine.

According to another specific embodiment, the psychotropic drug is an adrenergic effector such as dihydroergotamine, modafinil, adrafinil, mirtazapine and oxetorone.

According to another specific embodiment, the psychotropic drug is an acetylcholinergic effector such as sulbutiamine, tropatepin or trihexyphenidyl.

According to another specific embodiment, the psychotropic drug is a serotoninergic effector such as chlorpromazine, trimipramine, clozapine, olanzapine, cyamemazine, flupentixol, nefopam, fluvoxamine, clomipramine, sertraline, fluoxetine, citalopram, escitalopram, paroxetine, amitriptyline, duloxetine, venlafaxine, buspirone, carpipramine, zolmitriptan, sumatriptan, naratriptan, indoramine, ergotamine, ergotamine tartrate, pizotifene, pipamperone, methysergide, pizotyline, tianeptine, milnacipran, amitriptyline, trimipramine, viloxazine, tianeptine, hypericum and lithium.

According to another specific embodiment, the psychotropic drug is an opioidergic effector such as nalbuphine, buprenorphine, pethidine, codeine, tramadol, morphine, hydromorphone, oxycodone, methadone, dextropropoxyphene, meperidine, fentanyl, naltrexone or morphine hydrochloride.

According to another specific embodiment, the psychotropic drug is an adenosinergic effector such as carbamazepine or oxcarbazepine.

According to another specific embodiment, the psychotropic drug is an ionotropic effector such as flunarizine, ethosuximide, levetiracetam, lamotrigine, fosphenytoin or phenytoin.

According to another specific embodiment, the psychotropic drug is a histaminergic effector such as niaprazine, hydroxyzine or doxylamine.

According to another specific embodiment, the psychotropic drug is a monoamine oxidase effector such as moclobemide, selegiline or iproniazid.

According to another specific embodiment, the psychotropic drug is a catechol-O-methyl transferase effector such as entacapone or tolcapone.

According to another specific embodiment, the psychotropic drug is a DOPA decarboxylase effector such as benserazide or carbidopa.

According to another specific embodiment, the psychotropic drug is a noradrenergic effector such as mianserine, desipramine, moclobemide or bupropion.

According to another specific embodiment, the psychotropic drug is an effector acting on the limbic system, such as gabapentin or captodiamine.

Even more preferably, the psychotropic molecule chosen is clozapine, a dibenzodiazepine derivative, or paroxetine, escitalopram, sertraline or venlafaxine, which are serotoninergic effectors or any other serotoninergic effector such as chlorpromazine, trimipramine, olanzapine, cyamemazine, flupentixol, nefopam, fluvoxamine, clomipramine, fluoxetine, citalopram, amitriptyline, duloxetine, buspirone, carpipramine, zolmitriptan, sumatriptan, naratriptan, indoramine, ergotamine tartrate, pizotifene, pipamperone, methysergide, pizotyline or tianeptine.

Even more preferably, the psychotropic molecule chosen is modafinil, a diphenylmethane derivative, which is an adrenergic effector or any other adrenergic psychotropic effector such as dihydroergotamine, adrafinil, mirtazapine or oxetorone.

Thus, even more preferably, the psychotropic molecule is chosen from: modafinil, clozapine, paroxetine, diazepam, venlafaxine, escitalopram, bupropion or sertraline.

In a preferred embodiment, the psychotropic molecule is an antidepressant chosen from: moclobemide (MOCLAMINE), amitriptyline (LAROXYL), clomipramine (ANAFRANIL), milnacipran (IXEL), escitalopram (SEROPLEX), citalopram (SEROPRAM), fluoxetine (PROZAC), paroxetine (DEROXAT), fluvoxamine (FLOXYFRAL), sertraline (ZOLOFT), mitrapazine (NORSET), duloxetine (Cymbalta) or venlafaxine (EFFEXOR) and bupropion (ZYBAN).

In an even more preferred embodiment, the psychotropic molecule is an antidepressant chosen from the group including: paroxetine, venlafaxine, escitalopram, bupropion and sertraline.

According to a third aspect, this invention also relates to the use of this product in combination, simultaneously, separately or sequentially, in patients with psychiatric and/or neurodegenerative disorders.

Patients needing this treatment may have psychiatric and/or neurodegenerative disorders included in the group consisting of: depression, bipolar disorder, epilepsy, schizophrenia, generalized anxiety, depression, conditions due to stress, panic, phobias, obsessive compulsive disorders, behavioral disorders, immune system depression, fatigue and symptoms associated with pain, chronic fatigue, fibromyalgia, and other disorders such as autism, attention deficit, hyperactivity, eating disorders such as bulimia, anorexia, obesity, psychic disorders such as apathy, migraine, pain, cardiovascular diseases, neurodegenerative disorders and disorders associated with depressive anxiety (Alzheimer's disease, Huntington's disease, Parkinson's disease), drug dependence and drug addiction.

In the case of simultaneous use, the two components of the treatment are administered to the patient simultaneously. According to this embodiment of the present invention, the two components can be packaged together, in the form of a mixture, or separately, then mixed spontaneously before being administered together to the patient. More commonly, the two components are administered simultaneously, but separately. In particular, the routes of administration of the two components may be different. The administration can also be performed at different sites. In another embodiment, the two components are administered sequentially or spaced apart over time, for example in the same day or at an interval ranging from several hours to several weeks, or even several months.

According to a fourth aspect, this invention involves the use of at least one connexin-blocking agent for preparing a drug intended to be administered before, at the same time, or after a psychotropic drug, in order to treat a patient suffering from psychiatric and/or neurodegenerative disorders.

According to a fifth aspect, the invention includes the use of at least one connexin-blocking agent, for modulating and/or potentiating the effect of a psychotropic drug in patients with psychiatric and/or neurodegenerative disorders.

The term "modulate" in this case means intervening, by potentiation or antagonism, on the direct or indirect effects of the psychotropic drug administered before, simultaneously or after the anti-connexin agent, in particular on the adverse effects.

The term "potentiate" in this case means significantly increasing the effects of the psychotropic drug administered before, simultaneously or after the anti-connexin agent. Thus, the combination of the psychotropic drug with the anti-connexin agent makes it possible to reduce the doses of said psychotropic drug and therefore to limit the adverse effects of said psychotropic drug, and/or to reduce the effects of failure and withdrawal.

The invention therefore also relates to the use of at least one connexin-blocking agent, for reducing the doses of said psychotropic drug and/or limiting the adverse effects of said psychotropic drug, and/or reducing the effects of failure and withdrawal.

According to a final aspect, the invention describes a method for treating a patient with psychiatric and/or neurodegenerative disorders, including the administration to said patient of:

a) at least one active substance selected from the psychotropic drugs, and b) at least one connexin-blocking agent, and in which said products a) and b) are administered simultaneously, separately or spread out over time.

EXAMPLES

The analysis of the domains of the brain by electroencephalography is today considered to be a reliable and very sensitive technique for characterizing the effects of a drug on the central nervous system. Electroencephalography (EEG) is the measurement of the electrical activity of the brain by means of electrodes placed on the scalp, often represented in the form of a line called the electroencephalogram. Comparable to the electrocardiogram, which makes it possible to study the functioning of the heart, the EEG is a painless and noninvasive examination that provides information on the neurophysiologic activity of the brain over time and in particular of the cerebral cortex, either for a diagnostic neurological purpose or for cognitive neuroscience research purposes. The electric signal at the basis of the EEG is the resultant, for each frequency, of the summation of the synchronous post-synaptic action potentials produced by a large number of neurons.

It has been demonstrated that the electrical power associated with each frequency can vary independently of that of the others as a function of the individual's behavior or the drug administered (Dimpfel W, Neuropsychobiology. 1986: 15(2): 101-8). After administration of a drug, the electroencephalogram of the patient changes, and the distribution of the potentials associated with each frequency constitutes the electropharmacogram of said drug. In general, the electropharmacograms are different for drugs prescribed for different diseases, and are similar when they are intended to treat the same pathologies (Dimpfel W, British Journal of Pharmacology, 2007, 152, 538-548). Electropharmacograms corresponding to more than 150 drugs have been determined (for example, analgesics, antidepressants, neuroleptics, stimulants, tranquilizers, sedatives and narcotics). Today, after these numerous studies, the determination and the analysis of the electropharmacogram is considered to be a reliable technique for measuring the pharmacological effects of a drug. In addition, the parameters of the EEG make it possible to obtain quantitative information on the development in the clinical phase of numerous compounds (Mandema & Danhof, Clin. Pharmacokinet. 1992, 23, 191-215). The measurement of the EEG potential can also be used to identify the cell receptors of the drugs administered (Parker T J, British Journal of Pharmacology 2001, 132, 151-158). The EEG is a measurement of the electrical activity of the brain and there are different modes for representing electroencephalographic data. The first is the representation of the lines and the identification of characteristic undulation phenomena. This qualitative data is informative for clearly determined episodes of electrical activity, but does not provide information on the quantitative aspect of the electrical activity. For this, the experimenter uses the quantitative EEG based on the analysis of the Fourier transform signal making it possible to obtain power values for a given frequency over time. This power value is associated with a control value that makes it possible to determine the power modification for a given frequency over time. This value may be averaged by time periods variable according to the experiments. These power variations over time may be represented according to the authors either in the form of averages over specific frequency ranges corresponding to physiological or pathological rhythms (Delta (1-4 Hz), Theta (4.5-8 Hz), Alpha (8.5-12 Hz), Beta (12.5-24 Hz) and Gamma (>24 Hz)), or in the form of relative power histograms, Hz-by-Hz. These two representation modes are strictly equivalent, one being derived from the other (see EEG: Bases neurophysiologiques, principes d'interpretation et de prescription Jean Vion-Dury, France Blanquet. Editor: MASSON; Collection: Abrégé Masson). In the examples presented below, the representation of the relative powers Hz-by-Hz has been chosen.

With regard, for example, to atypical antipsychotics, and in particular clozapine, it has been demonstrated that their administration causes a biphasic electropharmacogram over time: during the first hour, the EEG potential is very high for very low frequencies (between 0.8 and 4.5 Hz) (delta rhythm) and between 7 and 9.5 Hz (alpha rhythm I), and low intensity at frequencies between 4.75 and 6.75 Hz (theta rhythm) and greater than 18.5 Hz (beta rhythm), which is the sign of a positive clinical response (Galderisi S, Methods Find Exp Clin Pharmacol, 2002, 24, 85-89). In the second hour, the EEG potential is at average intensity on frequencies ranging from 8 to 15 Hz, which can involve extrapyramidal side effects. Indeed, an EEG potential of average intensity in the second hour for frequencies of 7-9.5 Hz and 12.75-18.50 Hz means that adverse effects will be present (Dimpfel W, British Journal of Pharmacology 2007, 152, 538-548).

Protocol:

Pre-Implantation of Electrodes

A group of 6 conscious Wistar rats was pre-implanted with 6 bipolar bilateral electrodes (2 frontal, 2 anterior hippocampic, 2 posterior hippocampic).

Injections

Different treatments were conducted by circular combination of 6 rats by treatment (psychotropic treatment alone, anti-connexin treatment alone, anti-connexin+psychotropic combination treatment). The injection of meclofenamic acid (Sigma) is performed by slow submeningeal injection (80 ng/kg, 4.5 pg/second) or intraperitoneally at different doses. The injection of glycyrrhetinic acid (Sigma) is performed by submeningeal injection (80 ng/kg). The injection of clozapine (Sigma) is performed intraperitoneally (0.2 mg/kg). The injection of paroxetine (Sigma) is performed intraperitoneally (0.5 mg/kg). The injection of modafinil (Cephalon) is performed intraperitoneally (125 mg/kg and 250 mg/kg).

Measurement of the EEG

The EEG measurements were performed on the different groups of conscious rats (previously implanted and habituated) by 2-hour recordings after injection. The spectral analysis performed by Fourier transform (FFT) makes it possible to obtain relative powers, Hertz-by-Hertz and second-by-second. The FFT data is then averaged minute-by-minute and associated with the solvent control produced the day prior to the recording under strictly identical experimental conditions. The relative spectral powers of the left and right prefrontal cortices are then averaged by 5-minute periods, averaged by groups of 12 5-minute repetitions and represented hour-by-hour.

Statistical Analyses:

The data obtained from the relative quantitative EEG analysis of the effects of the different drugs administered individually (psychotropic alone or anti-connexin agents alone), presented in the examples, were subjected to a statistical analysis by analysis of variance (ANOVA) with three factors: "Frequency" (by Hz), "Time" (first and second hour by 12 averaged 5-minute repetitions) and "Animal" (6 different animals for each treatment). For the combinations of psychotropic and anti-connexin agents presented in the examples, a fourth ANOVA factor was introduced: "Anti-connexin combination". The significance threshold of the relative power modifications for a given frequency for a psychotropic drug alone with respect to the control (solvent of the psychotropic agent) or a psychotropic drug in combination with an anti-connexin with respect to the psychotropic agent administered alone (in favor of a relative power increase or a decrease) was chosen at a value of $P<0.05$.

Example 1

Effects of Connexin Inhibitors

A series of experiments for studying the influence of connexins in the EEG activity of different brain structures was performed. For this, the cerebral connexins were inhibited, by slow administration, directly submeningeal, of a connexin inhibitor, meclofenamic acid (MFA). Under the same experimental conditions, the effects of the intracerebral administration of glycyrrhetinic acid (BGA), another anti-connexin agent, were studied.

Figure 1:
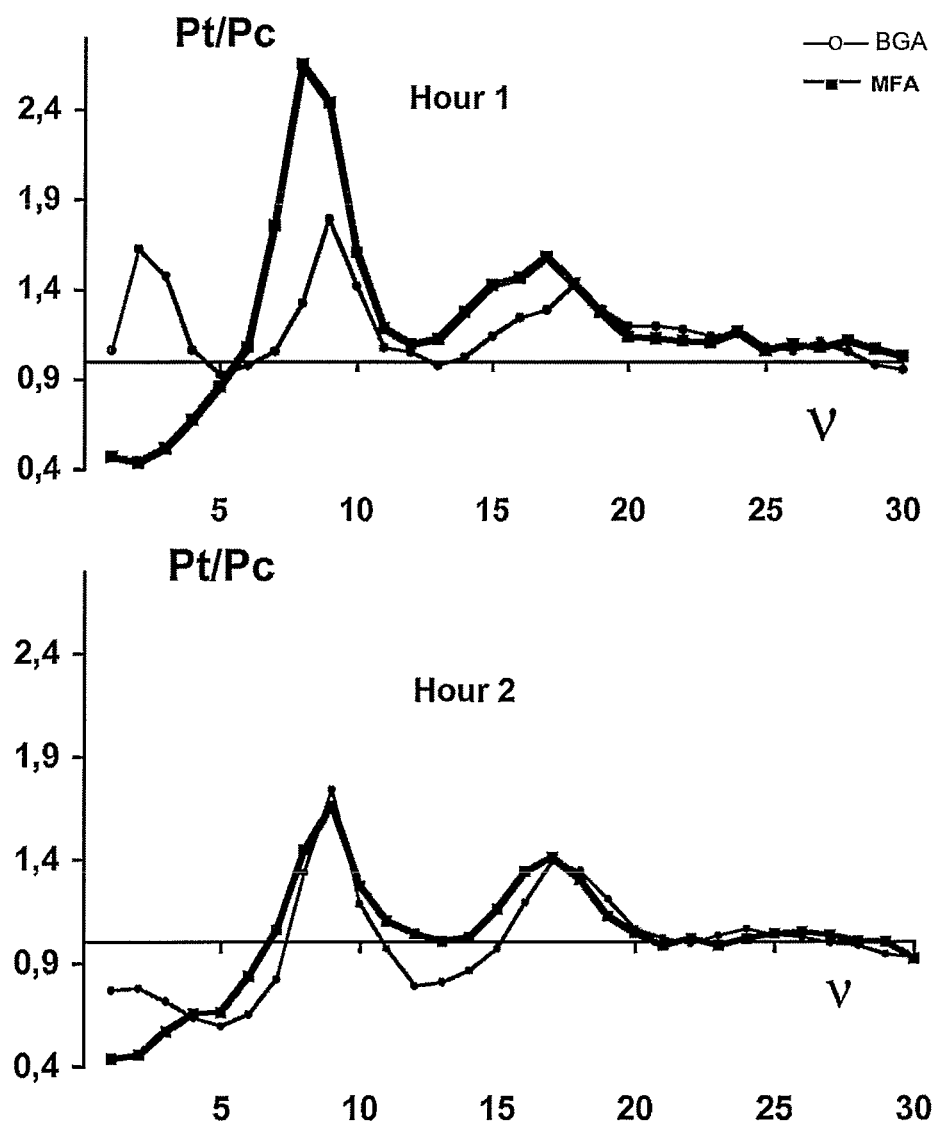
FIG. 1 shows the spectral analysis of the electrical activity of the prefrontal cortex by quantitative EEG of the effect of submeningeal injection of Meclofenamic acid (MFA, black squares) or 18-β-Glycyrrhetinic acid (Beta GA, white circles). The x-axis shows the frequencies analyzed and the y-axis shows the relative powers obtained from the FFT analysis. The spectral analysis is shown as an average for the first hour and for the second hour of recording.

The analysis of the cerebral electrical activity in rats treated with the connexin inhibitor (MFA) intracerebrally shows a significant increase in the EEG potential and therefore in the synchronization of the prefrontal cerebral activity (140%) for frequencies of 8-10 Hz, at the first hour and extending to the second hour. Similar significant modifications are observed in the intracerebral injection of another anti-connexin class (glycyrrhetinic acid) (FIG. 1).

This synchronization indicates that the connexins have a physiological role of desynchronizing electrical activities. In consideration of the overall effect of the connexin inhibitors on the different regions studied and the ubiquitous presence of junctions comprised of connexins in the brain, these experimental results make it possible to reinterpret the data in the literature and to propose an unreported role of the connexins in the normalization of electrophysiological activities of the brain. This normalization would be intended to circumscribe the electrical activity burst phenomena and to modulate and damp anarchic dysfunctioning of the highly interconnected system.

Example 2

Effect of an Atypical Antipsychotic in Combination with a Connexin Inhibitor

To explore the hypothesis of a general modulating role on connexins in cerebral activity, the electrophysiological consequences of a pharmacological treatment combined with anti-connexin molecules were studied.

In this context, the effects of clozapine in combination with a connexin-inhibitor, meclofenamic acid (MFA), were studied. Clozapine is an atypical antipsychotic indicated for schizophrenia, a serotoninergic and dopaminergic receptor antagonist, alternatively an adrenergic, cholinergic and histaminergic antagonist having a typical complex EEG activation spectrum (Parker T J, *British Journal of* Pharmacology 2001, 132, 151-158) and a considerable list of adverse effects at therapeutic doses (weight gain, decrease in bone marrow and number of leukocytes in the blood).

2.1 Effect of Clozapine

In a first phase, the experimental model was validated so as to verify that it was in agreement with the published data (Dimpfel W, *British Journal of Pharmacology* 2007, 152, 538-548, Parker T J, *British Journal of Pharmacology* 2001, 132, 151-158). Recordings of the effect of clozapine alone were therefore produced.

Figure 2:
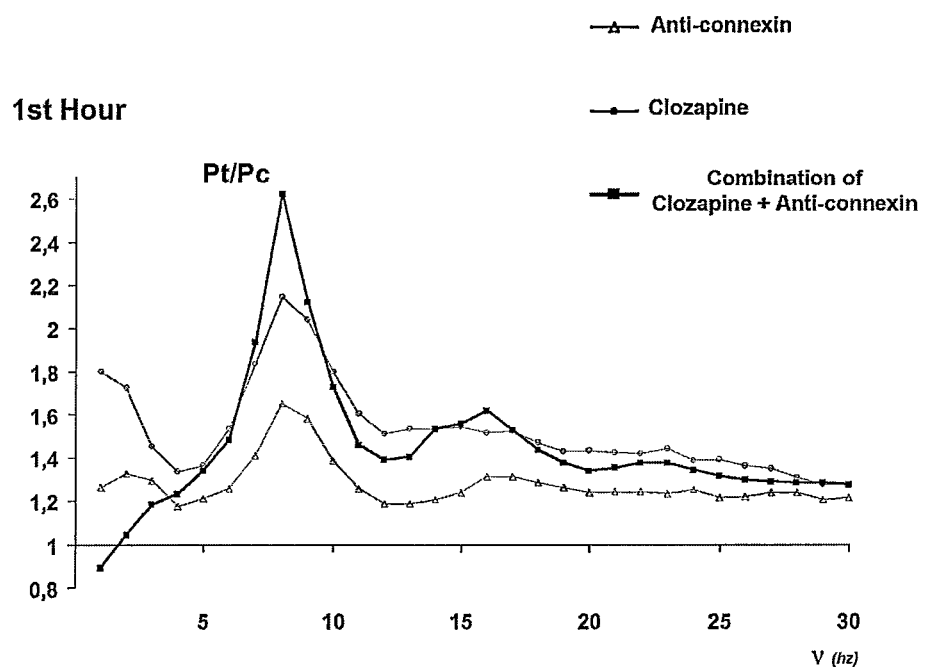
FIG. 2 shows the spectral analysis of the electrical activity of the prefrontal cortex by quantitative EEG of the effect of Clozapine alone (0.2 mg/kg intraperitoneally), the connexin inhibitor alone (Meclofenamic acid, 80 ng/kg per submeningeal injection), or the combination [Clozapine and connexin inhibitor]. The x-axis shows the frequencies analyzed and the y-axis shows the relative powers obtained from the Fourier transform analysis (FFT). The spectral analysis is shown as an average for 6 animals for the first hour (top) and the second hour (bottom).
Figure 2:
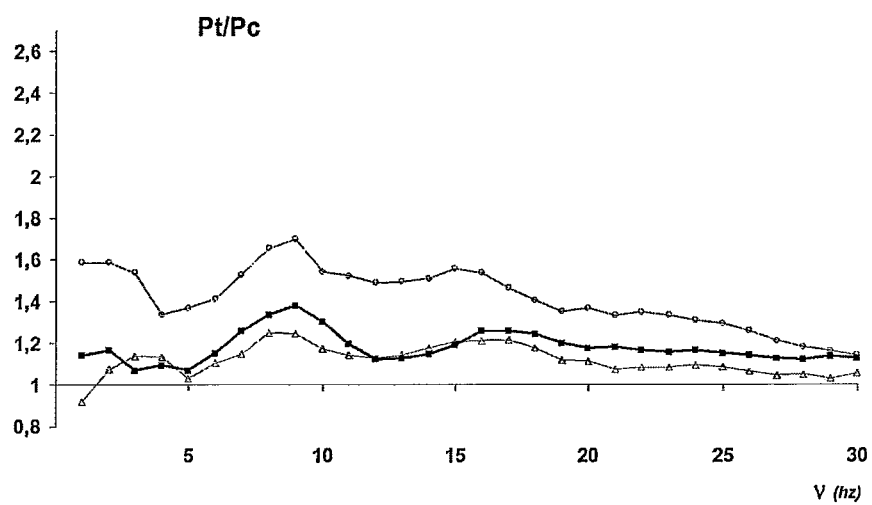

The spectral analysis of the EEGs shows a significant increase in the EEG potential, and therefore in the synchronization of the prefrontal cerebral activity (200%) for frequencies of 8-10 Hz and to a lesser extent for frequencies of 16-20 Hz during the treatment with the antipsychotic alone, from the first hour and extending to the second hour (FIG. 2).

These observations are completely consistent with the characteristic effects of atypical antipsychotics reported in the literature (Dimpfel W, *British Journal of Pharmacology* 2007, 152, 538-548, Parker T J, *British Journal of Pharmacology* 2001, 132, 151-158).

2.2 Effect of the Clozapine and Anti-Connexin Combination

In a second phase, the influence of the connexin junction system on the electrophysiological effect of clozapine was studied.

During the treatment combining the antipsychotic (clozapine) and the connexin inhibitor (MFA), the spectral analysis of the EEGs shows a significant increase in the synchronization of the prefrontal cerebral activity (260%) for frequencies of 8-10 Hz and to a lesser extent for frequencies of 16-20 Hz at the first hour. This significant increase in synchronization corresponds to the clozapine spectrum and therefore corresponds to a potentiation of the effect of clozapine by blocking of the connexin junction system. This mechanism of reinforcement of the effect of clozapine by the anti-connexin is controlled over time. Indeed, at the second hour, only the anti-connexin effect persists (FIG. 2).

Figure 3:
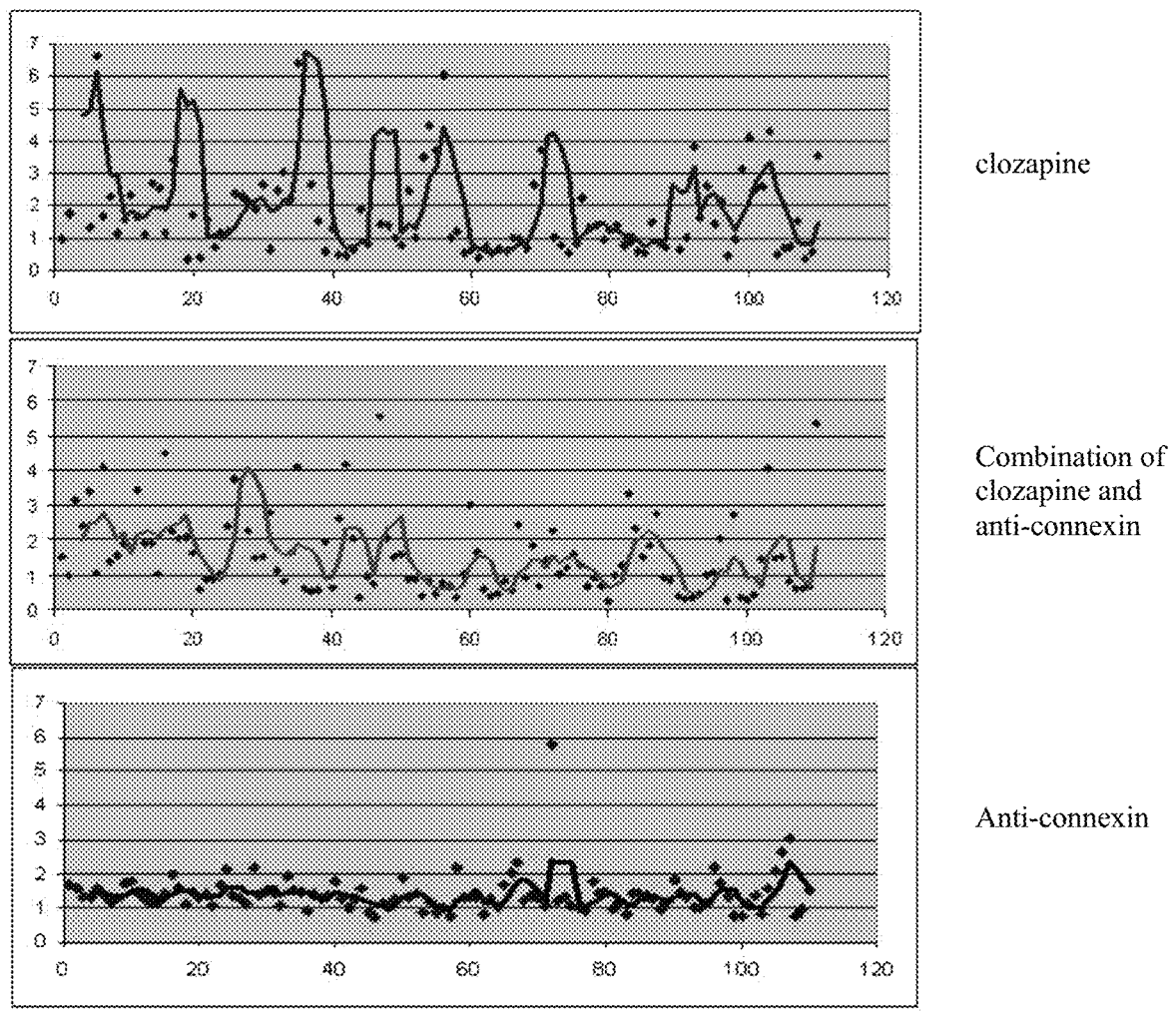
FIG. 3 shows an analysis of the change minute-by-minute in the prefrontal cortex with an average frequency of 8 Hz by quantitative EEG of the effect of Clozapine alone (0.2 mg/kg intraperitoneally), the connexin inhibitor alone (Meclofenamic acid, 80 ng/kg per submeningeal injection) or the combination [Clozapine and connexin inhibitor]. The x-axis shows the time in minutes and the y-axis shows the relative powers obtained in the FFT analysis.

In addition, by focusing the analysis on a significant frequency (the frequency of 8 Hz, for example), the reinforcement of the effect of clozapine observed is accompanied by a considerable damping of the amplitude of the oscillation effects (FIG. 3), while the treatment with clozapine alone causes high-amplitude fluctuations (FIG. 3).

Thus, the damping of the fluctuations caused by clocking of the connexin junction system means that the connexins may play a role in the establishment of these brief fluctuations in electrophysiological activity. These fluctuations would correspond to quick activity kindling mechanisms produced the clozapine and controlled by the connexins.

Finally, these results confirm the hypothesis of a modulating role (in overall intensity and on local and time-based fluctuations) of the electrophysiological activities by the connexin junction system. Moreover, these observations demonstrate an unreported modulation in the antipsychotic effect due to its combination with a connexin inhibitor. This modulation is manifested by the significant potentiation and stabilization of the antipsychotic effect over a shorter period. This potentiation of the effect of the antipsychotic would be identical to that obtained with a higher dose of clozapine, but with a control on the duration of action.

Example 3

Comparison of Administration Routes

The electrophysiological consequences of the blocking of connexins according to the central or peripheral (intracerebral vs. intraperitoneal) route of administration of the MFA inhibitor were compared.

Figure 4:
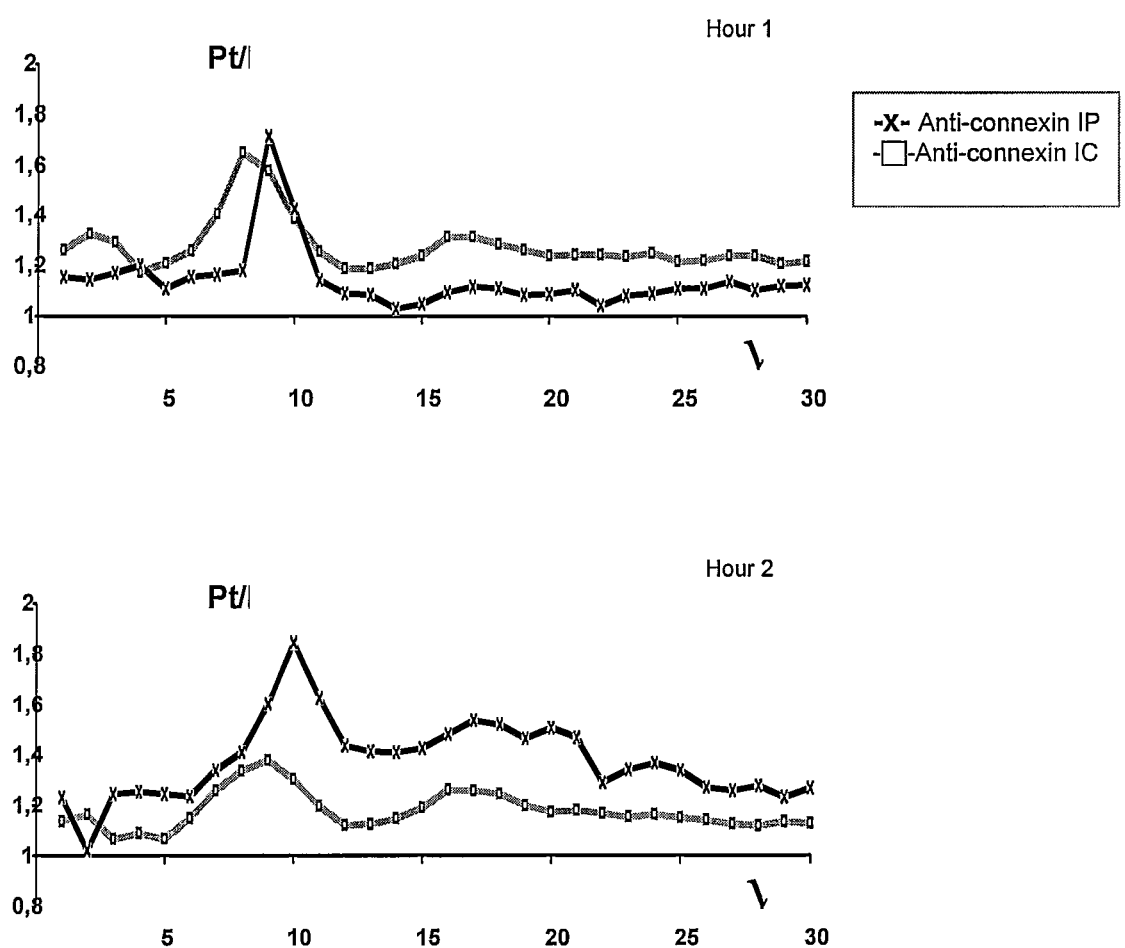
FIG. 4 shows the spectral analysis of the electrical activity of the prefrontal cortex by quantitative EEG of the effect of the connexin inhibitor by submeningeal injection (Meclofenamic acid, 80 ng/kg), or by intraperitoneal injection (Meclofenamic acid, 2.45 mg/kg). The x-axis shows the frequencies analyzed and the y-axis shows the relative powers obtained from the FFT analysis. The spectral analysis is shown as an average for 6 animals for the first hour and for the second hour of recording.

The spectral analysis of the EEGs, evaluating the peripheral and central routes of administration, shows a significant increase comparable to the synchronization of the prefrontal cerebral activity at the first hour and for similar frequency ranges. However, the significant increase in synchronization continues at the second hour for peripheral administration, whereas it decreases for central administration. This difference at the second hour is associated with the pharmacokinetics of the administration routes (FIG. 4).

Finally, these preliminary results indicate that the route of administration, whether intracerebral or peripheral, modifies the effect only in amplitude.

Example 4

Effect of Different Doses of Anti-Connexin Administered Intraperitoneally

The electrophysiological consequences of the blocking of connexins according to the peripherally administered dose administered of the MFA inhibitor were compared (dose-effect).

Figure 5:
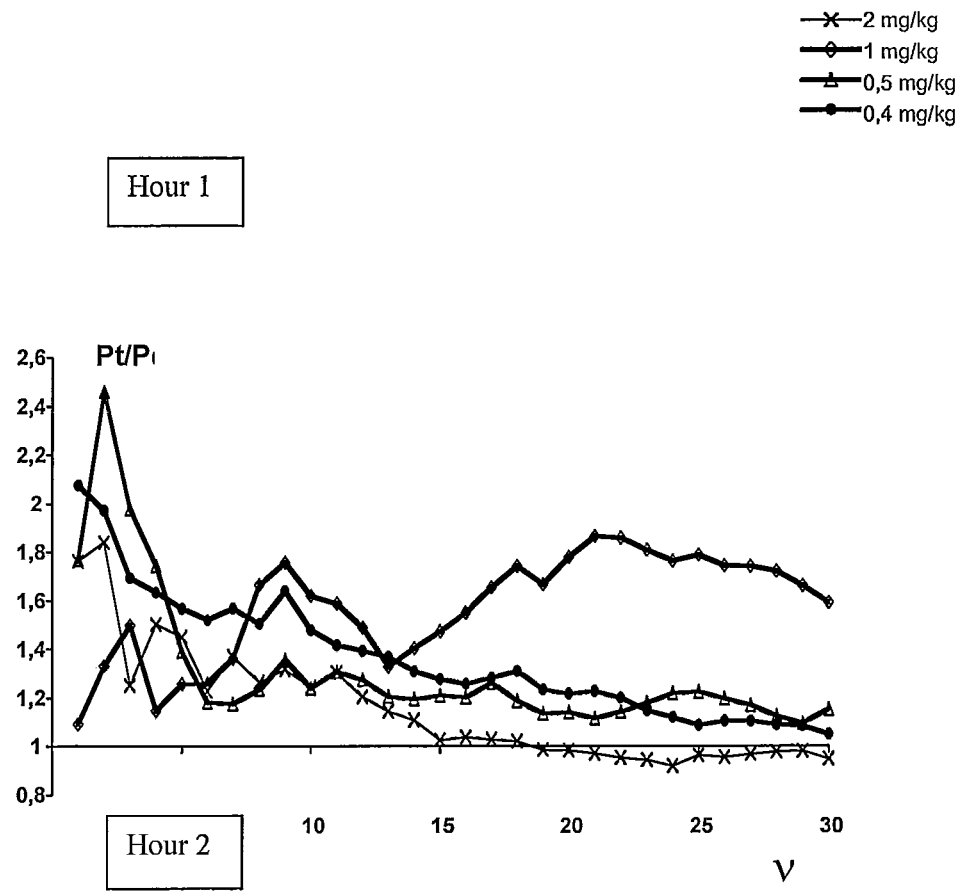
FIG. 5 shows the spectral analysis of the electrical activity of the prefrontal cortex by quantitative EEG of the effect of different doses of the connexin inhibitor by intraperitoneal injection (Meclofenamic acid, 2 mg/kg, 1 mg/kg, 0.5 mg/kg, 0.4 mg/kg). The x-axis shows the frequencies analyzed and the y-axis shows the relative powers obtained from the FFT analysis. The spectral analysis is shown as an average for the first hour and for the second hour of recording.
Figure 5:
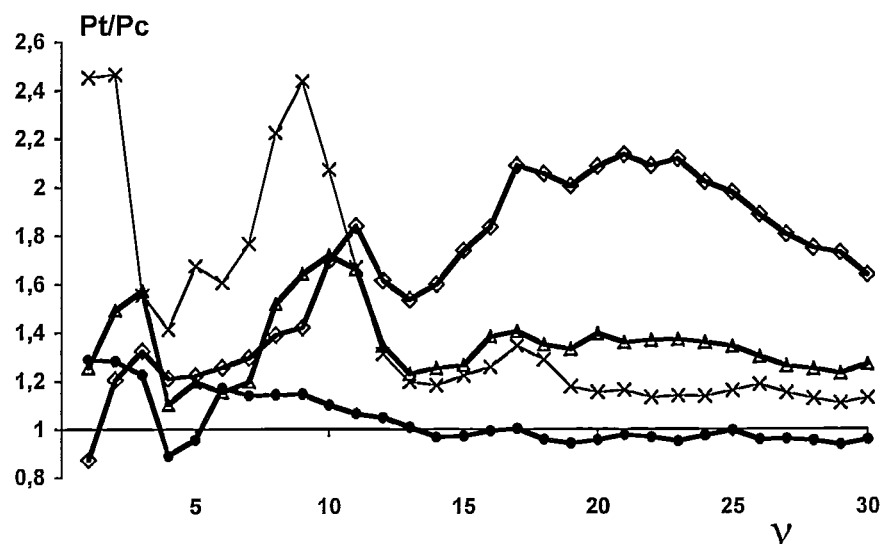

The spectral analysis of the EEGs, evaluating the doses administered peripherally, shows important significant variations in synchronization on different frequency ranges according to the dose. These modifications in favor of synchronization of the prefrontal cerebral activity appear at the first hour and continue to the second hour variably according to the dose. This synchronization by inhibition of the connexins confirms the physiological desynchronizing character of the connexins (FIG. 5). These important synchronizations according to the dose may be due to the quantitative representation (number of variable gap junctions according to the central nervous system network, ex: cholinergic, noradrenergic, serotoninergic, etc.) and/or qualitative representation (affinity of the different connexin isoforms for the inhibitor at the given dose) of connexins.

On the whole, these preliminary results indicate that the specific effects of anti-connexins administered intraperitoneally are dependent on the dose. This appears to indicate that this system of modulation via connexins, even if it is ubiquitous in the brain, has local specificities (in isoform or quantity) in the brain, which is consistent with the literature (Fukuda T., *Neuroscientist* 2007; 13(3): 199-207). This also means that, according to the system specifically targeted by the psychotropic drug (cholinergic, serotoninergic, noradrenergic, GABAergic, etc.), according to its structure and its chemical properties, and according to its pharmacology (half-life, metabolism, clearance), the anti-connexin dose should clearly be adapted.

Finally this dose-effect study made it possible to identify the MFA dose administered intraperitoneally which causes the minimum actual EEG effect (no significant modification at the first hour, slight significant increase at the second hour), compatible with the exploration of the potentiation of the effects of different psychotropic agents. This MFA dose is 0.4 mg/kg (dose 10 to 25 times smaller than the dose used for anti-inflammatory effects) and will be the dose used for the potentiation examples described in examples 5 and 6.

Example 5

Effect of a First Antidepressant in Combination with a Connexin Inhibitor

To continue the evaluation of the hypothesis of a modulating role of connexins in cerebral activity, the electrophysiological consequences of a first pharmacological antidepressant treatment combined with anti-connexin molecules were studied.

In this context, the effects of paroxetine in combination with a connexin inhibitor, meclofenamic acid (MFA), were studied. Paroxetine is an antidepressant, indicated for acute or chronic depressive episodes, derived from phenylpiperidine of the selective serotonin reuptake inhibitor group and having a considerable list of adverse effects at the therapeutic doses (apathy, pupil dilation, nausea, teratogenicity, somnolence, headaches, weight and appetite changes, changes in sexual behavior, increase in feelings of depression and anxiety, dry mouth, aggressive behavior (in particular in children), possible congenital deformations, erythema, psychomotor instability, itching, depletion (sodium), sweating, suicidal ideation, muscle weakness, muscle pain, unusual levels of aggression, serotonin syndrome).

5.1 Effect of Paroxetine

In a first phase, the experimental model was evaluated because no bibliographic data on the EEG effect of paroxetine in the conscious rat is available. However, various studies on the effects of paroxetine, in particular on sleep-wake rhythms provide the pharmacological doses of paroxetine for acute treatment, which are generally 2 to 5 mg/kg (Sanchez C, *Pharmacol Biochem Behav.* 2007 March; 86(3):4 68-76).

Recordings of the effect of paroxetine alone were therefore produced at a dose of 0.5 mg/kg administered intraperitoneally (4 to 10 times less than the dose normally used in an acute treatment in the rat).

Figure 6:
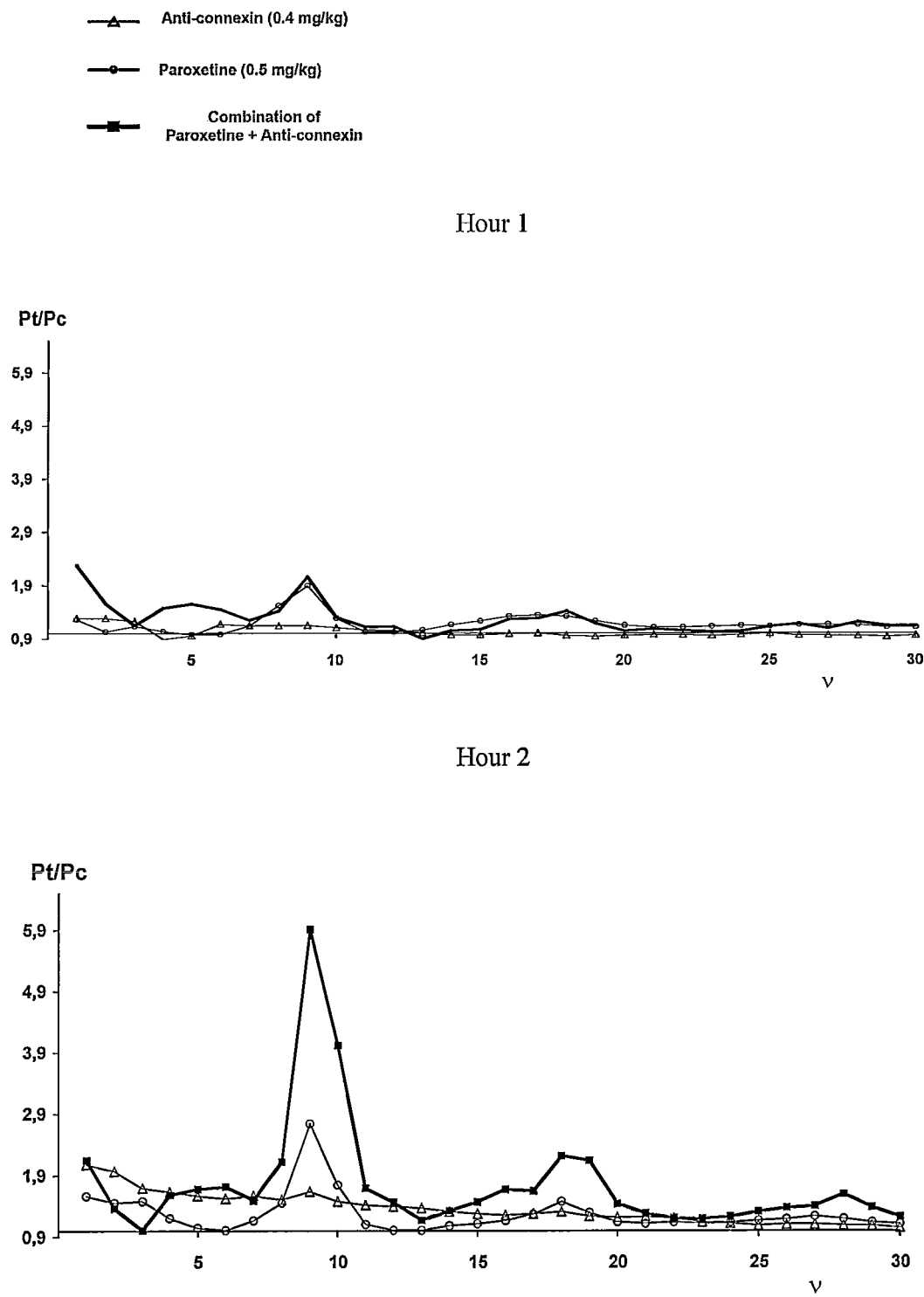
FIG. 6 shows the spectral analysis of the electrical activity of the prefrontal cortex by quantitative EEG of the effect of Paroxetine (0.5 mg/kg intraperitoneally) alone, the connexin inhibitor (Meclofenamic acid, 0.4 mg/kg by intraperitoneal injection) alone, or the combination of Paroxetine and connexin inhibitor. The x-axis shows the frequencies analyzed and the y-axis shows the relative powers obtained from the FFT analysis. The spectral analysis is shown as an average for 6 animals for the first hour and for the second hour.

The spectral analysis of the EEGs shows a significant increase in the relative powers in the prefrontal cortex, and therefore in the synchronization of the prefrontal cerebral activity (around 200%) at 8-10 Hz and to a lesser extent for frequencies of 2-3 Hz and 18-19 Hz in the treatment with the antidepressant alone, at the first hour and increasing (around 300%) at the second hour for frequencies of 8-10 Hz and to a lesser extent for frequencies of 2-3 Hz and 18-19 Hz (FIG. 6).

5.2 Effect of the Combination of Paroxetine and Anti-Connexin

In a second phase, the influence of the connexin junction system on the electrophysiological effect of paroxetine was studied.

In the treatment combining the antidepressant (paroxetine) and the connexin inhibitor (MFA), the spectral analysis of the EEGs shows a significant increase in the synchronization of the prefrontal cerebral activity (600%) for frequencies of 8-10 Hz and to a lesser extent for frequencies of 2-3 Hz and 18-19 Hz at the second hour. This significant increase in synchronization corresponds perfectly to the spectrum for paroxetine alone and therefore corresponds to a considerable potentiation of the effect of paroxetine by blocking the connexin junction system. In addition, this mechanism of reinforcement of the effect of paroxetine by the anti-connexin follows the same time course as the paroxetine alone. Indeed, paroxetine alone or in combination with the anti-connexin causes EEG effects that increase at the second hour and that must wear off several hours after administration (FIG. 6).

Thus, unlike clozapine, which causes a maximum EEG activity at the first hour, paroxetine produces effects that are more prolonged over time and that take more time to develop. The potentiation by the anti-connexin therefore retains the time course properties of the psychotropic molecules studied (of different chemical natures, targeting different systems and with very different indications) and reinforces the notion of a system of modulation by connexins that is not limited to a single neurotransmission system.

On the whole, these results confirm the hypothesis of an electrophysiological activity modulating role (on overall intensity and time course) by the connexin junction system.

Finally, these observations show an unreported modulation in the antidepressant effect by the combination of the antidepressant with a connexin inhibitor. This modulation is manifested by the potentiation of the antidepressant effect at a dose 4 to 25 times smaller than the pharmacological dose. This potentiation in the antidepressant effect by the anti-connexin would therefore make it possible to reduce the antidepressant doses by 4 to 25 times, with a minimum effect specific to the anti-connexin. The measured dose benefit of the paroxetine and anti-connexin combination would therefore be greater than 4.

Example 6

Effect of a Psychostimulant in Combination with a Connexin Inhibitor

To continue the evaluation of the hypothesis of an overall modulating role of connexins in cerebral activity, the electrophysiological consequences of a psychostimulant pharmacological treatment combined with anti-connexin molecules were studied.

In this context, the effects of modafinil (provigil) in combination with a connexin inhibitor, meclofenamic acid (MFA), were studied. Modafinil is a psychostimulant, indicated for the treatment of narcolepsy and idiopathic hypersomnia, a noradrenaline reuptake inhibitor with a list of adverse effects at therapeutic doses (excitation, aggressiveness, insomnia, anorexia, headaches, nausea, stomach ache, allergic skin eruptions).

6.1 Effect of Modafinil

In a first phase, the experimental model was evaluated with the published data providing in particular the pharmacological doses of modafinil in an acute treatment, which are generally 100 to 350 mg/kg (Sebban C, *British Journal of Pharmacology* (1999) 128, 1045-1054, De saint Hilaire Z., *Neuroreport*. 2001 Nov. 16; 12(16): 3533-7). Recordings of the effect of modafinil alone at two doses (125 and 250 mg/kg) were therefore produced.

Figure 7:
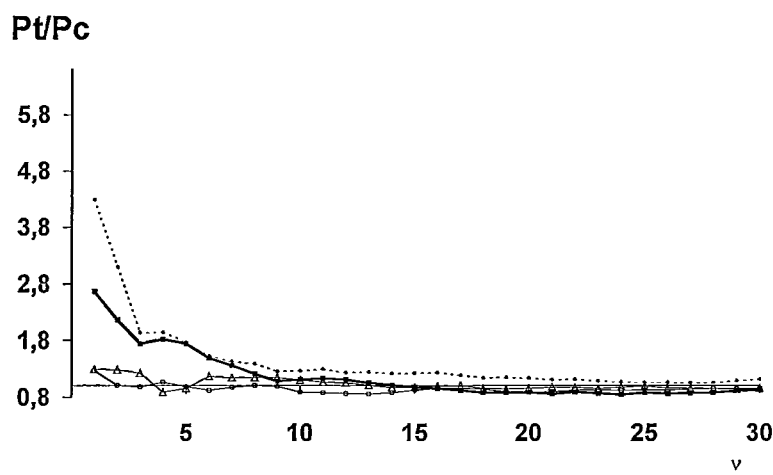
FIG. 7 shows the spectral analysis of the electrical activity of the prefrontal cortex by quantitative EEG of the effect of Modafinil (125 mg/kg and 250 mg/kg intraperitoneally)
Figure 7:
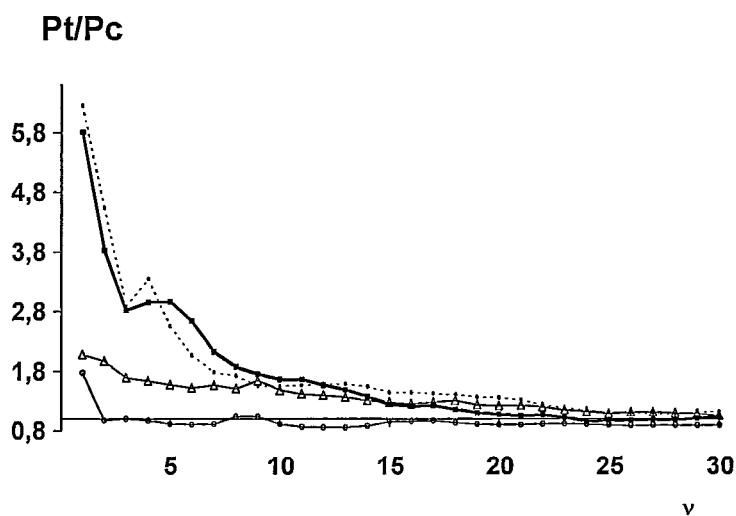

The spectral analysis of the EEGs shows a significant increase in the EEG potential, and therefore in the synchronization of the prefrontal cerebral activity (300% the 250 mg/kg dose and 120% for the 125 mg/kg dose) for frequencies of 2-5 Hz and a significant decrease in the EEG potential, and therefore a desynchronization in the prefrontal cerebral activity (10 to 30%) for frequencies of 10-25 Hz for the 125 mg/kg dose and to a lesser extent for the 250 mg/kg dose for the treatment with the psychostimulant alone, at the first hour and increasing at the second hour (FIG. 7).

These observations are compatible with the characteristic psychostimulant effects reported in the literature (Sebban C, *British Journal of Pharmacology* (1999) 128, 1045-1054, De saint Hilaire Z., *Neuroreport*. 2001 Nov. 16; 12(16): 3533-7).

6.2 Effect of the Combination of Modafinil and Anti-Connexin

In a second phase, the influence of the connexin junction system on the electrophysiological effects of modafinil at a low dose (125 mg/kg) was studied.

In the treatment combining the psychostimulant (modafinil) and the connexin inhibitor (MFA), the spectral analysis of the EEGs shows a significant increase in the synchronization of the prefrontal cerebral activity (300%) for frequencies of 2-5 Hz and to a lesser extent a significant reduction in the EEG potential, and therefore desynchronization of the prefrontal cerebral activity for frequencies of 10-25 Hz at the first hour and increasing at the second hour (FIG. 7). These EEG modifications completely correspond to the spectrum of modafinil alone at the high dose (250 mg/kg) and therefore correspond to a potentiation of the effect of modafinil by blocking of the connexin junction system. In addition, like clozapine and paroxetine, this mechanism of reinforcement of the effect of modafinil by the anti-connexin follows the same time course as modafinil alone at a higher dose. This potentiation by the anti-connexin retaining the time course properties of psychotropic agents of very different types again confirms the notion of a system of modulation by connexins that is not limited to a single neurotransmission system.

On the whole, these results confirm the hypothesis of a modulating role (on overall intensity and on the time course) of the electrophysiological activities by the connexin junction system. Moreover, these observations show an unreported modulation of the psychostimulant effect by the combination with a connexin inhibitor. This modulation is manifested by the potentiation of the psychostimulant effect at a low dose and perfectly mimics the effects of a high dose. This potentiation of the effect of the psychostimulant by the anti-connexin would therefore make it possible to reduce the psychostimulant doses by a factor of at least two, without any effect specific to the anti-connexin. The measured dose benefit of the modafinil and anti-connexin combination would therefore be at least two.

Example 7

Effect of an Anxiolytic in Combination with a Connexin Inhibitor

To continue the evaluation of the hypothesis of an overall modulating role of the connexins on cerebral activity, the electrophysiological consequences of an anxiolytic pharmacological treatment combined with an anti-connexin molecule were studied.

In this context, the effects of diazepam in combination with a connexin inhibitor, meclofenamic acid (MFA) were studied. Diazepam is an anxiolytic, indicated for excessive anxiety episodes, sleeping difficulties, neurotic states, psychosomatic manifestations, alcohol detoxification and epilepsy. Diazepam is a benzodiazepine facilitating GABAergic transmission, with a considerable list of adverse effects at therapeutic doses (somnolence, hypotonia, feeling of intoxication, difficulty concentrating, irritability, aggressiveness, excitation, confusion, hepatitis, allergic skin reactions, dysphagia) and can lead to tolerance and dependence requiring a dosage adjustment during the various phases of the treatment.

7.1 Effect of Diazepam

In a first phase, the experimental model was evaluated in order to compare it with the bibliographic data on the EEG effect of diazepam administered intraperitoneally in the conscious rat (Robledo P., *Alcohol Clin Exp Res*. 1994 April; 18(2)-363-8). Recordings of the effect of diazepam alone were therefore produced at the 1 mg/kg dose administered intraperitoneally (1.5 to 5 times less than the dose normally used in an acute treatment in the rat).

The spectral analysis of the EEGs shows, at the first hour, the characteristic effects of diazepam, namely a slight decrease in power of the 4-7 Hz components (around 25% decrease) and a significant increase in the power of the 11-30 Hz components (around 120%). At the second hour, these effects on the 4-7 Hz and the 11-30 Hz components persist while reducing in intensity and a significant increase in the power of the 1-3 Hz components appears (cf. FIG. 8).

7.2 Effect of the Combination of Diazepam and Anti-Connexin

After having validated the experimental model, the influence of the connexin junction system on the electrophysiological effect of diazepam was studied.

In the treatment combining the anxiolytic (diazepam, 1 mg/kg intraperitoneally) and the connexin inhibitor (MFA, 0.4 mg/kg intraperitoneally), the spectral analysis of the EEGs shows, at the first hour, a significant increase in the power for the 11-30 Hz components (around 150%) and the 1-3 Hz components (around 120%). This increase in power continues at the second hour with a higher amplitude for the 11-30 Hz components (up to 200%) (cf. FIG. 8).

This significant increase in the power of 1-3 Hz and 11-30 Hz components corresponds to the spectrum of diazepam alone at higher doses (2 to 10 times the dose used in the first test) and therefore corresponds with a considerable potentiation of the effect of diazepam by blocking of the connexin junction system. In addition, unlike diazepam alone, the potentiation by the anti-connexin reinforces the effect at the second hour, indicating an action extended over time in the presence of anti-connexin. This latter observation differs from the effect of the anti-connexin molecules in combination with clozapine, modafinil and paroxetine by not exactly following the time course of the diazepam alone, indicating that the system of modulation by the connexins may be quantitatively different from one neurotransmission system to the other. Thus, in the case of diazepam, the blocking of the junction system would have a stronger influence at the second hour than at the first, emphasizing that, according to the organization of the junction system in the chemical neurotransmission systems, the blocking will have different qualitative and quantitative consequences.

On the whole, this potentiation of the GABAergic system confirms the hypothesis of a modulating role (likely qualitatively and quantitatively dependent on the organization in the chemical neurotransmission systems) on the electrophysiological activities by the connexin junction system.

Finally, these results show an unreported modulation of the anxiolytic effect by the combination of the drug with a connexin inhibitor. This modulation is manifested by a potentiation of the anxiolytic effect which, at a dose 2 to 10 times smaller than the pharmacological dose, makes it possible to obtain, when combined with the anti-connexin molecule, the same electroencephalographic effect as the pharmacological dose alone. This potentiation of the anxiolytic effect by the anti-connexin would therefore make it possible to reduce the anxiolytic doses by 2 to 10 times, and with a minimal effect specific to the anti-connexin. The measured dose benefit of the combination of diazepam and the anti-connexin would therefore be greater than 2.

Example 8

Effect of a Second Antidepressant in Combination with a Connexin Inhibitor

To continue the evaluation of the hypothesis of an overall modulating role of the connexins on cerebral activity, the electrophysiological consequences of a second antidepressant pharmacological treatment combined with anti-connexin molecules were studied.

In this context, the effects of venlafaxine in combination with a connexin inhibitor, meclofenamic acid (MFA) were studied. Venlafaxine is an antidepressant, indicated for major depressive episodes in adults, the prevention of recurrent depression in patients with a unipolar disorder, and generalized anxiety for at least 6 months in adults. Venlafaxine is a serotonin and noradrenaline reuptake inhibitor, with an intermediate profile, and with an efficacy comparable to that of the imipramines, and has a considerable list of adverse effects at therapeutic doses (nausea, somnolence, dry mouth, insomnia, vertigo, constipation, sweating, hyponatremia, difficulty ejaculating, diarrhea, vomiting, weight gain, headaches, agitation, shaking, paresthesia, palpitations, accommodation disorder, skin eruptions) and can cause a withdrawal syndrome when the treatment is stopped.

8.1 Effect of Venlafaxine

In a first phase, the experimental model was evaluated with venlafaxine alone, because no bibliographic data on the EEG effect of venlafaxine in the conscious rat is available; however, various studies on the effects of venlafaxine, in particular on sleep modifications, provide the pharmacological doses of venlafaxine in acute treatment, which are generally from 1 to 10 mg/kg administered intraperitoneally (Salin-Pascual R J., *Psychopharmacology*. 1997 February; 129 (3): 295-6).

Recordings of the effect of venlafaxine alone were conducted at two doses, 0.16 mg/kg and 4 mg/kg administered intraperitoneally (1 to 25 times less than the dose normally used in an acute treatment in the rat).

The spectral analysis of the prefrontal EEGs shows a significant increase in power, according to the venlafaxine dose, of the 8-10 Hz components (around 120% for the 0.16 mg/kg dose and 200% for the 4 mg/kg dose) and 16-18 Hz components and to a lesser extent the 24-26 Hz components at the first hour and increasing at the second hour with the appearance of an increase in the power of 1-3 Hz components at 4 mg/kg (FIG. 9).

8.2 Effect of the Combination of Venlafaxine and Anti-Connexin

Next, the influence of the connexin junction system on the electrophysiological effect of venlafaxine was studied.

In the treatment combining the antidepressant (venlafaxine, 0.16 mg/kg intraperitoneally) and the connexin inhibitor (MFA, 0.4 mg/kg intraperitoneally), the spectral analysis of the EEGs shows, at the first hour, a significant increase in the power for the 8-10 Hz components (around 350%), 16-18 Hz components (around 200%) and 24-26 Hz components (around 180%). This increase in power continues at the second hour with a decrease in amplitude for the different components (primarily for the 8-10 Hz components) except for the 1-3 Hz components, for which a significant increase in power is observed (cf. FIG. 9).

This significant increase in synchronization corresponds to the spectrum of venlafaxine alone, and therefore corresponds to a considerable potentiation of the effect of venlafaxine by blocking of the connexin junction system. In addition, unlike venlafaxine alone, the potentiation by the anti-connexin reinforces the effect at the first hour and decreases at the second hour (while remaining higher than the venlafaxine treatment alone), indicating a quick action that extends over time in the presence of anti-connexin. This latter observation is similar to the observation of the results of the combination with diazepam and differs from the effect of the anti-connexin molecules in combination with clozapine, modafinil and paroxetine by not exactly following the time course of the venlafaxine alone, confirming that the system of modulation by the connexins may be quantitatively different from one neurotransmission system to the other. Thus, in the case of venlafaxine, it is confirmed that the blocking of the junction system will have different qualitative and quantitative consequences according to its organization in the chemical neurotransmission systems.

On the whole, this potentiation of the serotoninergic and noradrenergic systems confirms the hypothesis of a major modulating role on the electrophysiological activities by the connexin junction system.

Finally, these results show an unreported modulation of the antidepressant effect by the combination of the antidepressant with a connexin inhibitor. This modulation is manifested by a potentiation of the antidepressant effect which, at a dose 25 times smaller than the pharmacological dose, makes it possible to obtain, when combined with the anti-connexin molecule, the same electroencephalographic effect as the antidepressant alone (at the pharmacological dose). This potentiation of the antidepressant effect by the anti-connexin would therefore make it possible to reduce the antidepressant doses by at least 25 times, and with a minimal effect specific to the anti-connexin. The measured dose benefit of the combination of venlafaxine and the anti-connexin would therefore be greater than 25.

Example 9

Effect of a Third Antidepressant in Combination with a Connexin Inhibitor

To continue the evaluation of the hypothesis of an overall modulating role of the connexins on cerebral activity, the electrophysiological consequences of a third antidepressant pharmacological treatment combined with anti-connexin molecules were studied.

In this context, the effects of escitalopram in combination with a connexin inhibitor, meclofenamic acid (MFA) were studied. Escitalopram is an antidepressant, indicated for major depressive states and the prevention of panic attacks with or without agoraphobia. Escitalopram is a serotonin reuptake inhibitor, with an intermediate profile, and with an efficacy comparable to that of the imipramines, and has a considerable list of adverse effects at therapeutic doses (nausea, headaches, insomnia, constipation, somnolence, sweating, difficulty ejaculating, diarrhea, vomiting, vertigo, trembling, paresthesia, palpitations, orthostatic hypotension and pruritis).

9.1 Effect of Escitalopram

In a first phase, the experimental model was evaluated because no bibliographic data on the EEG effect of escitalopram in the conscious rat is available; however, various studies on the effects of escitalopram, in particular on sleep EEG modifications, provide the pharmacological doses of escitalopram in acute treatment, which are generally from 1 to 10 mg/kg administered intraperitoneally (Sanchez C., *Pharmacol Biochem Behav.* 2007 March; 86(3): 468-76).

Recordings of the effect of escitalopram alone were conducted at two doses, 0.8 mg/kg and 4 mg/kg administered intraperitoneally (1 to 5 times less than the dose normally used in an acute treatment in the rat).

The spectral analysis of the prefrontal EEGs shows a significant increase in power, according to the escitalopram dose, of the 6-8 Hz components (around 150% for the 0.8 mg/kg dose and 200% for the 4 mg/kg dose) and 14-16 Hz components and to a lesser extent the 22-24 Hz components at the first hour and decreasing at the second hour (cf. FIG. 10).

9.2 Effect of the Combination of Escitalopram and Anti-Connexin

In a second phase, the influence of the connexin junction system on the electrophysiological effect of escitalopram was studied.

In the treatment combining the antidepressant (escitalopram, 0.8 mg/kg intraperitoneally) and the connexin inhibitor (MFA, 0.4 mg/kg intraperitoneally), the spectral analysis of the EEGs shows, at the first hour, a significant increase in the power for the 6-8 Hz components (around 450%), 14-16 Hz components (around 230%) and 22-24 Hz components (around 14%). This increase in power continues at the second hour with a decrease in amplitude for the different components (primarily for the 8-10 Hz components) (cf. FIG. 10).

This significant increase in synchronization fully corresponds to the spectrum of escitalopram alone, and therefore corresponds to a considerable potentiation of the effect of escitalopram by blocking of the connexin junction system. In addition, unlike clozapine, paroxetine and modafinil, this mechanism of reinforcement of the effect of escitalopram by the anti-connexin follows the same time course as escitalopram alone. Indeed, escitalopram alone or in combination with the anti-connexin produces EEG effects that are maximal at the first hour and that wear off at the second hour. Thus, the potentiation by the anti-connexin of escitalopram retains the time course properties and reinforces the notion of a system of modulation by the connexins that is not limited to a single neurotransmission system.

On the whole, this potentiation of the serotoninergic confirms the hypothesis of a modulating role on the electrophysiological activities by the connexin junction system.

Finally, these results again show the modulation of the antidepressant effect by the combination of the antidepressant with a connexin inhibitor. This modulation is manifested by a potentiation of the antidepressant effect which, at a dose 5 times smaller than the pharmacological dose, is capable, when combined with an anti-connexin molecule, of generating the same electroencephalographic effect as the antidepressant alone (at the pharmacological dose). This potentiation of the antidepressant effect by the anti-connexin would therefore make it possible to reduce the antidepressant doses by at least 5 times, and with a minimal effect specific to the anti-connexin. The measured dose benefit of the combination of escitalopram and the anti-connexin would therefore be greater than 5.

Example 10

Effect of a Fourth Antidepressant in Combination with a Connexin Inhibitor

To continue the evaluation of the hypothesis of an overall modulating role of the connexins on cerebral activity, the electrophysiological consequences of a fourth antidepressant pharmacological treatment combined with an anti-connexin molecule were studied.

In this context, the effects of bupropion in combination with a connexin inhibitor, meclofenamic acid (MFA) were studied. Bupropion is an antidepressant, indicated to help in smoking cessation in nicotine-dependent subjects. Bupropion is a noradrenaline and dopamine reuptake inhibitor, with a considerable list of adverse effects at therapeutic doses (skin eruption, pruritis, fever, nausea, headaches, insomnia, vertigo, constipation, vomiting, ataxia, tinnitus, mental confusion, visual disturbances).

10.1 Effect of Buproprion

In a first phase, the experimental model was evaluated because no bibliographic data on the EEG effect of bupropion in the conscious rat is available; however, various studies on the effects of bupropion, in particular on sleep EEG modifications, provide the pharmacological doses of bupropion in acute treatment, which are generally from 5 to 150 mg/kg administered intraperitoneally (Henshall D C, *Neuropsychiatr Dis Trat.* 2009; 5: 189-206).

Recordings of the effect of bupropion alone were conducted at three doses, 0.16 mg/kg, 0.8 mg/kg and 4 mg/kg administered intraperitoneally (10 to 150 times less than the dose normally used in an acute treatment in the rat).

The spectral analysis of the prefrontal EEGs shows a significant increase in power, according to the bupropion dose, of the 8-10 Hz components from 8-10 Hz (around 180% for the 0.16 mg/kg dose, 450% for the 0.8 mg/kg dose and 280% for the 4 mg/kg dose) and 15-18 Hz components and to a lesser extent the 23-25 Hz components at the first hour. At the second hour, a significant increase with respect to the first hour is observed for the same components for the doses 0.16 mg/kg and 4 mg/kg, while the effect wears off at the 0.8 mg/kg dose (FIG. 11).

This indicates an inverted "U-shaped" dose-effect of bupropion at the first hour (as shown in FIG. 13 for sertraline) and a classic dose-effect at the second hour.

These complex effects over time according to the dose suggest the involvement of different neurotransmission systems or neuron groups according to the bupropion dose.

10.2 Effect of the Combination of Bupropion and Anti-Connexin

In a second phase, the influence of the connexin junction system on the electrophysiological effect of bupropion was studied.

In the treatment combining the antidepressant (bupropion, 0.16 mg/kg intraperitoneally) and the connexin inhibitor (MFA, 0.4 mg/kg intraperitoneally), the spectral analysis of the EEGs shows, at the first hour, a significant increase in the power for the 8-10 Hz components (around 400%), components 15-18 Hz (around 230%) and 23-25 Hz components (around 140%). This increase in power continues at the second hour with a decrease in amplitude for the different components (primarily for the 8-10 Hz and 15-18 Hz components) (cf. FIG. 11).

This significant increase in synchronization corresponds to the spectrum of bupropion alone at the 0.8 mg/kg dose, and therefore indicates a considerable potentiation of the effect of bupropion by blocking of the connexin junction system. In addition, this mechanism of reinforcement of the effect of bupropion by the anti-connexin follows the same time course as bupropion alone at a higher dose, taking into account the complexity of the time course of the effects of bupropion according to the dose, mentioned above (paragraph 10.1). Indeed, bupropion alone at the 0.8 mg/kg dose or at the low dose (0.16 mg/kg) in combination with the anti-connexin produces EEG effects that are maximal at the first hour and that wear off at the second hour. Thus, the particular potentiation of bupropion by the anti-connexin confirms and reinforces the notion of a system of modulation by the connexins that is not limited to a single neurotransmission system.

On the whole, this potentiation of the noradrenergic and dopaminergic systems confirms the hypothesis of a modulating role on the electrophysiological activities by the connexin junction system.

Finally, these results again show the modulation of the effect of an antidepressant such as bupropion by the combination thereof with a connexin inhibitor. This modulation is manifested by a potentiation of the antidepressant effect which, at a dose 5 times smaller than the pharmacological dose, produces the same electroencephalographic effects as at the pharmacological dose when it is administered in combination with the anti-connexin molecule. This potentiation of the antidepressant effect by the anti-connexin would therefore make it possible to reduce the bupropion doses by at least 5 times, and with a minimal effect specific to the anti-connexin. The measured dose benefit of the combination of bupropion and the anti-connexin would therefore be greater than 5.

Example 11

Effect of a Fifth Antidepressant in Combination with a Connexin Inhibitor

To continue the evaluation of the hypothesis of an overall modulating role of the connexins on cerebral activity, the electrophysiological consequences of a fifth antidepressant pharmacological treatment combined with anti-connexin molecules were studied. In this context, the effects of sertraline in combination with a connexin inhibitor, meclofenamic acid (MFA), were studied.

Sertraline is an antidepressant, indicated for major depressive states in adults, obsessive compulsive disorders in adults and children, and the prevention of recurrent depression in patients with a unipolar disorder. Sertraline is a selective serotonin reuptake inhibitor, with a considerable list of adverse effects at therapeutic doses (skin rashes, pruritis, nausea, headaches, insomnia, vertigo, vomiting, extrapyramidal effect, difficulty ejaculating, constipation, visual disturbances, tachycardia).

11.1 Effect of Sertraline

In a first phase, the experimental model was evaluated because no bibliographic data on the EEG effect of sertraline in the conscious rat is available; however, various studies on the effects of sertraline, in particular on sleep EEG modifications, provide the pharmacological doses of sertraline in acute treatment, which are generally from 4 to 40 mg/kg administered intraperitoneally (Freo U., *Neurosci Lett.* 2008; 436(2): 148-52).

Recordings of the effect of sertraline alone were conducted at three doses, 0.16 mg/kg, 0.8 mg/kg and 4 mg/kg administered intraperitoneally (1 to 25 times less than the dose normally used in an acute treatment in the rat).

The spectral analysis of the prefrontal EEGs shows a significant increase in power, according to the sertraline dose, of the 7-9 Hz components (around 260% for the 0.16 mg/kg dose and the 0.8 mg/kg dose and 200% for the 4 mg/kg dose) and 14-17 Hz components and to a lesser extent the 23-25 Hz components at the first hour. At the second hour, a significant increase with respect to the first hour is observed for the same components for the 0.8 mg/kg (900%) and 4 mg/kg (450%) doses, while the effect wears off slightly at the 0.16 mg/kg dose (FIG. 12).

This indicates an inverted "U-shaped" dose-effect of sertraline primarily at the second hour (as shown in FIG. 13). These complex effects over time according to the dose, as in the case of bupropion, suggest the involvement of different neurotransmission systems or neuron groups according to the sertraline dose.

11.2 Effect of the Combination of Bupropion and Anti-Connexin

In a second phase, the influence of the connexin junction system on the electrophysiological effect of sertraline was studied.

In the treatment combining the antidepressant (sertraline, 0.16 mg/kg intraperitoneally) and the connexin inhibitor (MFA, 0.4 mg/kg intraperitoneally), the spectral analysis of the EEGs shows, at the first hour, a significant increase in power for the 7-9 Hz components (around 400%), 14-17 Hz components (around 300%) and 23-25 Hz components (around 160%). This increase in power continues at the second hour with a considerable increase in amplitude for the different components, primarily for the 7-9 Hz components (around 1000%) and 14-17 Hz components (around 700%) (FIG. 12).

This significant increase in synchronization at the second hour corresponds to the spectrum of sertraline alone at the 0.8 mg/kg dose, and therefore indicates a considerable potentiation of the effect of sertraline by blocking of the connexin junction system. In addition, this mechanism of reinforcement of the effect of sertraline by the anti-connexin follows the same time course as sertraline alone at a higher dose, in consideration of the complexity of the time course of the effects of sertraline according to the dose, mentioned above (paragraph 11.1).

Indeed, sertraline alone at the 0.8 mg/kg dose or at a lower dose (0.16 mg/kg) in combination with the anti-connexin agent, produces EEG effects that are maximal at the second hour. Thus, the particular potentiation of sertraline by the anti-connexin confirms and reinforces the notion of a system of modulation by the anti-connexins that is not limited to a single neurotransmission system.

On the whole, this potentiation of the serotoninergic system confirms the hypothesis of a modulating role on the electrophysiological activities by the connexin junction system.

Finally, these results again show the modulation of an antidepressant effect (sertraline) by the combination thereof with a connexin inhibitor. This modulation is manifested by a potentiation of the antidepressant effect at a dose 5 times smaller than the pharmacological dose. This potentiation of the antidepressant effect by the anti-connexin would therefore make it possible to reduce the antidepressant doses by at least 5 times, and with a minimal effect specific to the anti-connexin. The measured dose benefit of the combination of sertraline and the anti-connexin would therefore be greater than 5.

BIBLIOGRAPHY

Alldredge B T.: *J Clin Pathol*. May 12, 2008
Bai D, *J Pharmacol Exp Ther*, 2006 December; 319(3): 1452-8
Burt J M, et al, *Circ Research*. 1989; 65: 829-37
Chaytor A T et al, *J Physiol* 1997; 503: 99-110
Dahl G. et al, *Biophys J*, 1994; 67: 1816-22
De saint Hilaire Z., *Neuroreport*. 2001 Nov. 16; 12(16): 3533-7
Dimpfel W, *British Journal of Pharmacology* 2007, 152, 538-548
Fabrizi G M, *Brain* 2007 February, 130(Pt2): 394-403
Figueroa X F, Alvina K, Martinez A D, et al.: *Microvasc Res.* 2004; 68: 247-57
Freo U., *Neurosci Lett*. 2008; 436(2): 148-52
Fukuda T., *Neuroscientist* 2007; 13(3): 199-207
Galderisi S, *Methods Find Exp Clin Pharmacol*, 2002, 24, 85-89
Giepmans B N.: *Cardiovasc Res*. 2004; 62: 233-45
Guan X. et al, *J. Cell Biol* 1997; 139: 1785-92
Harks E G, *The Journal of Pharmacology and Experimental Therapeutics* 2001 September, 298(3): 1033-41
Harks E G, *The Journal of Pharmacology and Experimental Therapeutics* 2001 September, 298(3): 1033-41
Henshall D C, *Neuropsychiatr Dis Trat*. 2009; 5: 189-206
Hofer A et al, *Glia* 1998; 24: 141-54
Kale A Y 2006, *Brain Research Bulletin* 2006, Jul. 15; 135 (1-2): 1-6
Kola I, *Nat Rev Drug Discov*. 2004 August; 3(8): 711-5.
Lai-Cheong J E, Arita K & McGrath J A.: *J Invest Dermatol*. 2007; 127: 2713-25
Locke D. et al, *J Biol Chem* 2004; 279: 22883-92
Mandema & Danhof, *Clin. Pharmacokinet.* 1992, 23, 191-215
Meda P, *Médecine/Sciences* 1996; 12: 909-920
Meyer R A, *J. Cell Biol*. 1992; 119: 179-89
Negri L, *The Journal of Neuroscience*, 2006 Jun. 21; 26(25): 6716-27
Pan F, *Vis Neurosciences* 2007, July-August; 24(4): 609-18
Postma F R, *J Cell Biol* 1998 Mar. 9, 140(5): 1199-209
Robledo P., *Alcohol Clin Exp Res*. 1994 April; 18(2)-363-8
Salameh A, *Biochimica et Biophysica Acta* 1719 (2005) 36-58
Salin-Pascual R J., *Psychopharmacology*. 1997 February; 129(3): 295-6
Sanchez C., *Pharmacol Biochem Behav.* 2007 March; 86(3): 468-76
Scemes E, *Glia* 2008 Jan. 15, 56(2): 145-53
Sebban C, *British Journal of Pharmacology* 1999
Shaw R M, *Cell* 2007 Feb. 9, 128(3): 547-60
Srinivas M, *Molecular Pharmacology* 2003 June, 63(6): 1389-97
Srinivas M, *PNAS* 2001, 98: 10942-10947
Tejwani G A, *Brain Res*. 1998 Jun. 29; 797(2): 305-12
Wellershaus K, *Exp Cell Res*. 2008
Winneker R C, *Steroids*. 2003 November; 68(10-13): 915-20
Yao J, Hiramatsu N, Zhu Y, et al.: *J Am Soc Nephrol*. 2005; 16: 58-67;
Yao J, Morioka T & Oite T.: *Kidney Int*. 2000; 57: 1915-26.

The invention claimed is:

1. Method for treating patients suffering from one or more of depression; bipolar disorder; schizophrenia; anxiety; stress; panic; phobias; obsessive compulsive disorders; behavioral disorders; pain; fibromyalgia; eating disorders selected from the group consisting of bulimia and anorexia; migraine; and neurodegenerative disorders selected from the group consisting of Alzheimer's disease, Huntington's disease and Parkinson's disease, comprising the administration to said patients of:
   a) at least one psychotropic drug; and
   b) at least one connexin-blocking agent;
   the drug a) and the agent b) are administrated simultaneously, separately or spread out over time;
   wherein the at least one psychotropic drug is a serotoninergic effector selected from the group consisting of chlorpromazine, trimipramine, clozapine, olanzapine, cyamemazine, flupentixol, nefopam, fluvoxamine, clomipramine, sertraline, fluoxetine, citalopram, escitalopram, paroxetine, amitriptyline, duloxetine, venlafaxine, buspirone, carpipramine, zolmitriptan, sumatriptan, naratriptan, indoramine, ergotamine, ergotamine tartrate, pizotifene, pipamperone, methysergide, pizotyline, tianeptine, milnacipran, amitriptylene, trimipramine, viloxazine, tianeptine, hypericum, lithium, and combinations thereof,
   wherein the at least one connexin-blocking agent is selected from the group consisting of meclofenamic acid, 18-β-glycyrrhetinic acid, mefloquine, 2-APB and combinations thereof,
   wherein the at least one connexin-blocking agent is administered at a dose at least 10 to 25-fold less than a dose having an anti-inflammatory effect.

2. The method according to claim 1, wherein the serotoninergic effector is amitriptyline.

3. The method according to claim 1, wherein the serotoninergic effector is amitriptyline and the connexin-blocking agent is mefloquine.

* * * * *